(12) United States Patent
Otake

(10) Patent No.: US 12,042,608 B2
(45) Date of Patent: Jul. 23, 2024

(54) METHOD FOR INSERTING A CATHETER ASSEMBLY INTO A VESSEL USING A STORAGE CASE

(71) Applicant: TERUMO KABUSHIKI KAISHA, Tokyo (JP)

(72) Inventor: Yuya Otake, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 579 days.

(21) Appl. No.: 17/370,513

(22) Filed: Jul. 8, 2021

(65) Prior Publication Data

US 2021/0330930 A1 Oct. 28, 2021

Related U.S. Application Data

(60) Division of application No. 15/628,724, filed on Jun. 21, 2017, now Pat. No. 11,083,867, which is a
(Continued)

(30) Foreign Application Priority Data

Dec. 26, 2014 (JP) .................. 2014-264719

(51) Int. Cl.
*A61M 25/00* (2006.01)
*A61B 50/20* (2016.01)
(Continued)

(52) U.S. Cl.
CPC .......... *A61M 25/002* (2013.01); *A61M 39/18* (2013.01); *A61B 50/20* (2016.02);
(Continued)

(58) Field of Classification Search
CPC ........ A61M 25/002; A61M 2205/6081; A61M 2025/0174; A61B 50/30; B29L 2023/007
See application file for complete search history.

(56) References Cited

U.S. PATENT DOCUMENTS 4,607,746 A 8/1986 Stinnette
4,707,906 A 11/1987 Posey
(Continued)

FOREIGN PATENT DOCUMENTS

CN 2778309 Y 5/2006
CN 104023647 A 9/2014
(Continued)

OTHER PUBLICATIONS

International Search Report (PCT/ISA/210) issued on Mar. 8, 2016, by the Japanese Patent Office as the International Searching Authority for International Application No. PCT/JP2015/084814.
(Continued)

*Primary Examiner* — Andrew J Mensh
*Assistant Examiner* — Leah Jenna Anne Sibay
(74) *Attorney, Agent, or Firm* — BUCHANAN INGERSOLL & ROONEY PC

(57) ABSTRACT

A method for inserting a catheter assembly into a vessel using a storage case in which an outer pipe body and an inner pipe body which accommodate a guiding catheter and an inner catheter are connected to each other includes: pulling out the inner catheter from the inner pipe body, inserting the inner catheter into a proximal opening portion of the guiding catheter, causing a locking rotation portion of the inner catheter to rotate and be connected to a locking projection portion of the guiding catheter, assembling the guiding catheter and the pulled-out inner catheter, pulling-out, from the outer pipe body, the guiding catheter which is in a state where the inner catheter is assembled, taking out, from the storage case, a catheter assembly assembled by the guiding catheter and the pulled-out inner catheter, and inserting the catheter assembly into a vessel.

5 Claims, 22 Drawing Sheets

Related U.S. Application Data continuation-in-part of application No. PCT/JP2015/084814, filed on Dec. 11, 2015.

(51) Int. Cl.
*A61B 50/30* (2016.01)
*A61J 1/00* (2023.01)
*A61M 39/18* (2006.01)
*B65D 85/00* (2006.01)

(52) U.S. Cl.
CPC ............ *A61B 50/30* (2016.02); *A61J 1/00* (2013.01); *A61M 2025/0008* (2013.01); *A61M 2205/6081* (2013.01); *B65D 85/00* (2013.01)

(56) References Cited

U.S. PATENT DOCUMENTS

| | | | |
|---|---|---|---|
| 5,027,478 A | 7/1991 | Suhr | |
| 5,125,416 A * | 6/1992 | Phillips | A61B 50/30 600/585 |
| 5,163,554 A | 11/1992 | Lampropoulos et al. | |
| 5,242,428 A * | 9/1993 | Palestrant | A61M 25/01 604/265 |
| 5,309,604 A | 5/1994 | Poulsen | |
| 5,827,202 A | 10/1998 | Miraki et al. | |
| 6,375,006 B1 | 4/2002 | Samuels | |
| 6,511,573 B1 | 1/2003 | Globensky et al. | |
| 7,334,678 B2 | 2/2008 | Kesler et al. | |
| 7,461,741 B2 | 12/2008 | State et al. | |
| 9,789,277 B2 | 10/2017 | Suzuki et al. | |
| D809,136 S | 1/2018 | Kirwan | |
| 2005/0178684 A1* | 8/2005 | Kesler | A61M 25/002 206/364 |
| 2006/0011501 A1* | 1/2006 | Itou | A61M 25/002 206/370 |
| 2006/0278546 A1 | 12/2006 | State et al. | |
| 2006/0278547 A1* | 12/2006 | Rowe | A61M 25/002 206/363 |
| 2007/0185413 A1 | 8/2007 | Asai et al. | |
| 2010/0331821 A1* | 12/2010 | Itou | A61M 25/0041 604/533 |
| 2012/0022470 A1 | 1/2012 | Kuniyasu et al. | |
| 2012/0165680 A1* | 6/2012 | Akifumi | A61M 25/0662 600/466 |
| 2012/0181193 A1* | 7/2012 | Wu | B32B 27/28 206/204 |
| 2012/0203199 A1* | 8/2012 | Mann | A61M 39/0247 604/170.01 |
| 2012/0239005 A1* | 9/2012 | Conway | A61M 25/0017 604/544 |
| 2014/0262882 A1* | 9/2014 | Barnell | B29C 49/00 264/534 |
| 2014/0296782 A1 | 10/2014 | Ulrich et al. | |
| 2015/0068941 A1* | 3/2015 | Caron | A61M 25/002 206/364 |
| 2017/0209228 A1 | 7/2017 | Roberts et al. | |
| 2019/0262577 A1 | 8/2019 | Anderson | |

FOREIGN PATENT DOCUMENTS

| | | | | |
|---|---|---|---|---|
| JP | H11512949 A | | 11/1999 | |
| JP | 2007330548 A | | 12/2007 | |
| JP | 2012055601 A | | 3/2012 | |
| JP | 2013247974 A | * | 12/2013 | ......... A61M 25/002 |
| JP | 2013247974 A | | 12/2013 | |
| JP | 2014532524 A | | 12/2014 | |
| WO | 2005087304 A1 | | 9/2005 | |
| WO | WO-2005087304 A1 | * | 9/2005 | ......... A61B 5/15003 |
| WO | 2013098215 A1 | | 7/2013 | |
| WO | WO-2013098215 A1 | * | 7/2013 | ............ A61B 50/30 |

OTHER PUBLICATIONS

Written Opinion (PCT/ISA/237) issued on Mar. 8, 2016, by the Japanese Patent Office as the International Searching Authority for International Application No. PCT/JP2015/084814.

Office Action (Decision of Refusal) issued on Oct. 21, 2019, by the Japanese Patent Office in corresponding Japanese Patent Application No. 2016-566111 and an English Translation of the Office Action.

Office Action (First Office Action) issued on Dec. 16, 2019, by the State Intellectual Property Office of People's Republic of China in corresponding Chinese Patent Application No. 201580063241.3 and an English Translation of the Office Action.

The extended European Search Report issued on Jun. 27, 2018, by the European Patent Office in corresponding European Patent Application No. EP15872758.6-1132.

* cited by examiner

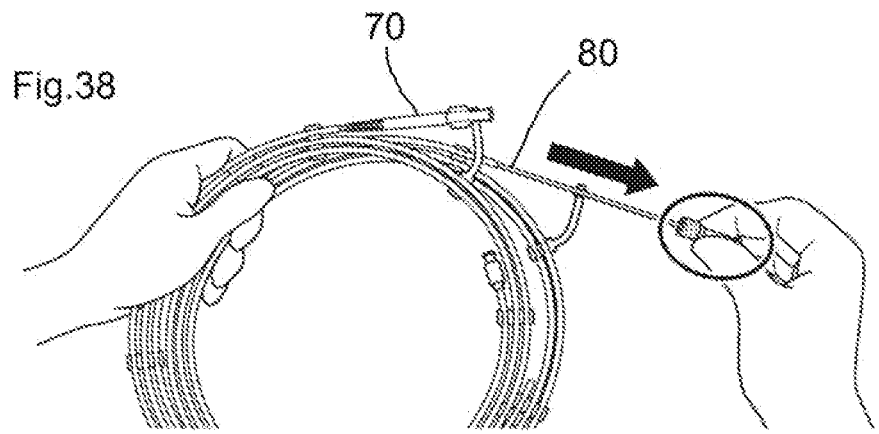
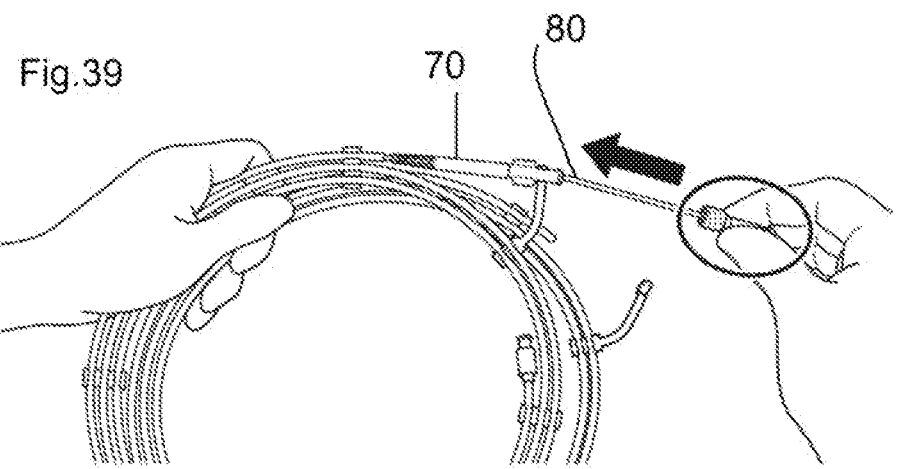

METHOD FOR INSERTING A CATHETER ASSEMBLY INTO A VESSEL USING A STORAGE CASE

CROSS-REFERENCES TO RELATED APPLICATIONS

This application is a divisional of U.S. application Ser. No. 15/628,724 filed on Jun. 21, 2017, which is a continuation-in-part of International Application No. PCT/JP2015/084814 filed on Dec. 11, 2015, and claims the benefit of JP2014-264719 filed on Dec. 26, 2014, the entire contents of each of which are incorporated herein by reference.

TECHNICAL FIELD

The present invention relates to a method for inserting a catheter assembly into a vessel using a storage case.

BACKGROUND ART

Known medical uses of a catheter which has been inserted into a lumen of a blood vessel or the like include, for example, administration of a contrast agent, a drug solution, or the like, as well as insertion and indwelling of a stent or the like in the lumen, via the inserted catheter. Such catheters have an elongated shape and are normally accommodated, for storage and transport, in a storage case having a predetermined shape. For example, JP-A-2012-55601 discloses a storage case for a catheter, with a holder as a pipe body that is wound to form a ring-like shape maintaining the shape with a connection member.

SUMMARY

In a case where a plurality of catheters, which are assembled when used, are packaged, similar to a guiding catheter and an inner catheter that is inserted in the guiding catheter, the catheters are individually packaged in a primary package case in a state in which the catheters are individually accommodated in holders as individual pipe bodies, respectively, and then the package cases are collectively packaged in a secondary package case such as a box. Hence, costs increase by the individual packages of the catheters, effort and time is required because an operator needs to open the individual primary package cases when the package cases are opened, and thus an environmental impact increases with an increase in waste.

An object of the present disclosure is to provide a storage case for a medical elongated body with which it is possible to reduce costs, to improve workability, and to reduce an environmental impact. The storage case accommodates a plurality of medical elongated bodies, which are assembled when used, and includes a plurality of pipe bodies wound to form a ring-like shape that are connected to each other in order to accommodate the medical elongated bodies, respectively.

Since the storage case having a configuration as described above includes the plurality of pipe bodies that are connected in order to accommodate the plurality of medical elongated bodies, respectively, which are assembled when used, the pipe bodies can be collectively accommodated in one package case. Therefore, it is possible to reduce costs with the medical elongated bodies not individually packaged, to reduce time and effort required for the opening of the package cases such that workability improves, and the waste is reduced such that it is possible to reduce an environmental impact.

A winding direction of the at least one pipe body is a direction opposite to the winding direction of the other pipe bodies. In this manner, the medical elongated body is pulled out from one pipe body with a portion between proximal opening portions of the pipe bodies, from which the medical elongated bodies are pulled out, grasped. Then, it is possible to easily assemble the pulled-out medical elongated body with another medical elongated body that is accommodated in another pipe body of which the proximal opening portion has an opposite direction without changing the grasped portion, and thus the operability improves.

The at least two pipe bodies have the same winding direction and have respective proximal opening portions, from which the respective medical elongated bodies are pulled out, on a same side of said storage case. In this manner, the medical elongated body is pulled out from one pipe body with a portion in the vicinity of the proximal opening portions of the pipe bodies grasped. Then, it is possible to easily assemble the pulled-out medical elongated body with another medical elongated body that is accommodated in another pipe body of which the proximal opening portion has the same direction without changing the grasped portion, and thus the operability improves.

The storage case further includes an assistive member for grasping the storage case. In this manner, it is possible to easily recognize the portion that is grasped and it is easy to perform grasping, and thus the operability improves.

At least two of the pipe bodies are disposed to overlap each other in a direction along the center axis of winding. In this manner, the overlapped pipe bodies are not disposed on the same plane. Therefore, it is possible to reduce the maximum outer diameter of the winding of the pipe body, it is possible to perform storage in a compact space, and a wide width is formed with the plurality of pipe bodies overlapped such that it is easy to hold the pipe body by hand. Further, opening portions of the pipe bodies can be close to each other in the portion that is grasped, it is easy to hold the pipe body by hand, and the operability improves.

One of the pipe bodies is an outer pipe body, and another one of the pipe bodies is an inner pipe body disposed on the center side of the winding of the outer pipe body. The medical elongated body, which is accommodated in the outer pipe body, is a guiding catheter. The medical elongated body, which is accommodated in the inner pipe body, is an inner catheter that is inserted into the inside of the guiding catheter. In this manner, it is possible to accommodate, in the outer pipe body, the guiding catheter, which is thin and is easily bent in a state in which the catheter has a curvature radius to the largest extent so as to provide a wide space in the inside thereof to the greatest extent.

The storage case further includes a plurality of connection members that connect the plurality of pipe bodies. The connection member, which is connected in the vicinity of the proximal opening portion from which the medical elongated body is pulled out, has a color different from that of the other connection member. In this manner, it is likely to easily recognize the portion of the storage case which is grasped, and thus the operability improves.

The storage case further includes a package case that collectively accommodates the plurality of connected pipe bodies. In this manner, it is possible to reduce costs without individual package of the medical elongated bodies, time and effort required for the opening of the package is reduced such that the workability improves, and the waste is reduced such that it is possible to reduce the environmental impact.

BRIEF DESCRIPTION OF THE DRAWINGS

FIG. 38 is a perspective view illustrating a fifth step in the method of taking out the guiding catheter and the inner catheter from the storage case according to the first embodiment.

FIG. 39 is a perspective view illustrating a sixth step in the method of taking out the guiding catheter and the inner catheter from the storage case according to the first embodiment.

DETAILED DESCRIPTION

Hereinafter, embodiments of the present invention will be described with reference to the figures. Note that a dimension ratio in the figures is enlarged and this is different from an actual ratio in some cases, depending on the description. In addition, in the specification, a "winding direction" of a pipe body that accommodates a medical elongated body means a direction in which from one end of the pipe body, at which a proximal opening portion from which the medical elongated body is pulled out is formed, and bending and winding is performed toward the other end portion on the opposite side. Note that the proximal opening portion of the pipe body is an opening portion on a side from which the medical elongated body accommodated in the pipe body is pulled out. In addition, a distal end opening portion of the pipe body is an opening portion provided at an end portion on the opposite side from the proximal opening portion of the pipe body.

Figure 1:
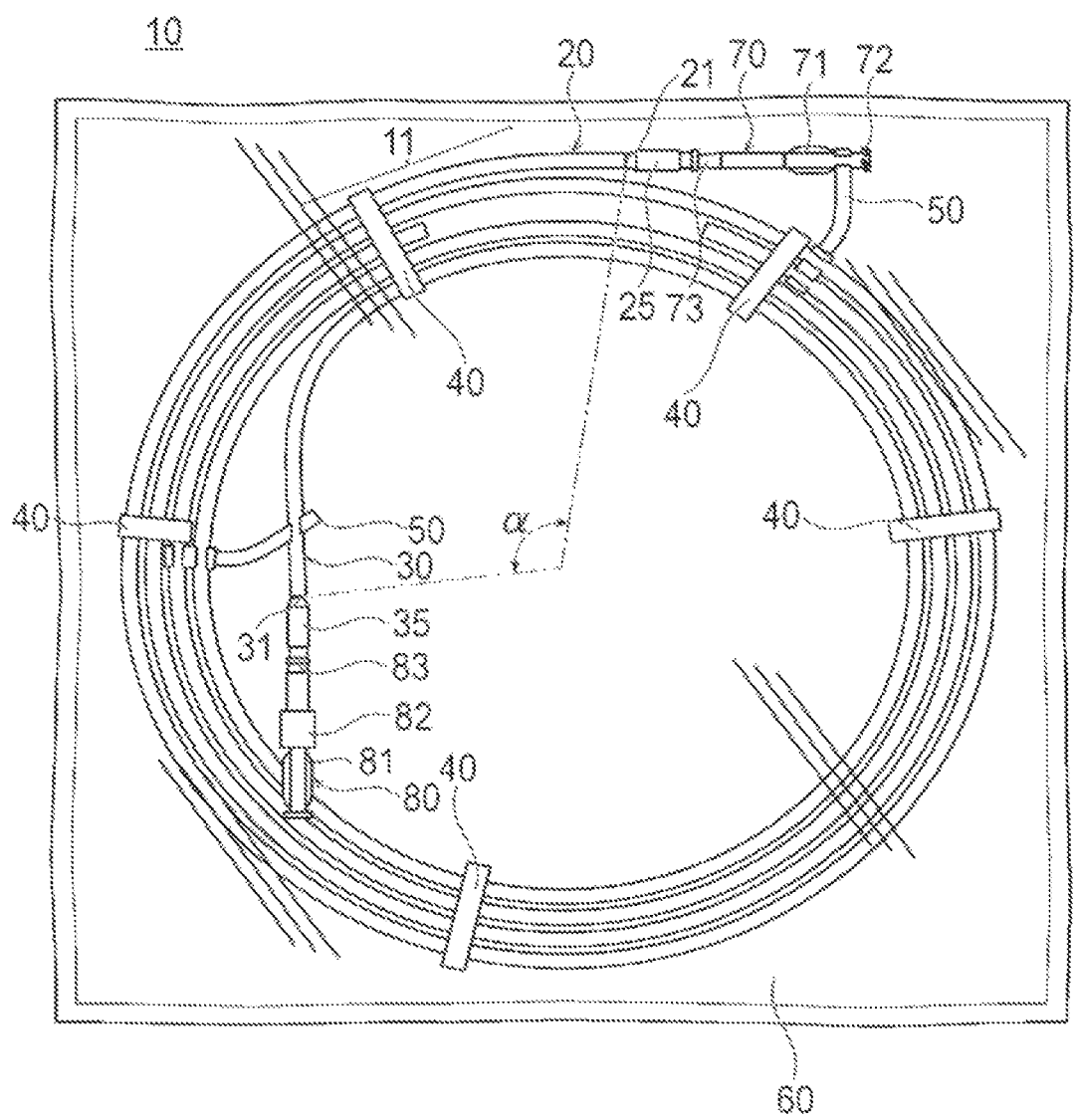
FIG. 1 is a plan view illustrating a storage case according to a first embodiment.

As illustrated in FIG. 1, a storage case 10 according to a first embodiment is a device that accommodates a guiding catheter 70 and an inner catheter 80 which are known and assembled when used, in order to store and carry the catheters. The guiding catheter 70 is a catheter for guiding to a lumen in the inside via the medical device such as a balloon catheter, and is thin to be folded so as to provide a wide space in the inside thereof to the largest extent. Therefore, in order to reduce the folding of the guiding catheter 70 when the guiding catheter 70 is inserted to a target position, the inner catheter 80 is inserted as a reinforcement member to the lumen of the guiding catheter 70. The guiding catheter 70 is provided with locking threads 72 of a rotation-locking type connector in a hub portion 71 into which the inner catheter 80 is inserted, and a hub portion 81 of the inner catheter 80 is provided with a locking rotation portion 82 having an inner peripheral surface on which a screw groove to which the locking thread 72 is screwed by rotation is provided. The inner catheter 80 is inserted into the guiding catheter 70 from a proximal portion of the guiding catheter 70, the locking rotation portion 82 is caused to rotate so as to engage with the locking thread 72, and thereby it is possible to maintain a state in which the inner catheter 80 is assembled to the guiding catheter 70.

Note that reasons why the guiding catheter 70 and the inner catheter 80, which are assembled when used, are not assembled until the catheters are used, include a possibility that insufficient sterilization will be performed, and a difficulty in priming in a gap between both catheters, with only slight gap formed between both, when the inner catheter 80 is inserted into the guiding catheter 70.

The storage case 10 includes an outer pipe body 20 (pipe body) that accommodates the guiding catheter 70, an inner pipe body 30 (pipe body) that accommodates the inner catheter 80, a connection member 40 for maintaining shapes of the outer pipe body 20 and the inner pipe body 30, a holding member 50 that holds a proximal portion of the guiding catheter 70, and a package case 60 that holds the catheters inside in a sterilized state. Note that the proximal portion of the catheter means a hand side on which an operator performs operation, as a side opposite to a portion that is inserted into a living body.

The outer pipe body 20 has a spiral shape as a whole, with a tube that extends by a predetermined length and is wound. The outer pipe body 20 holds the guiding catheter 70 so as to store and carry the catheter, with the guiding catheter 70 inserted through an outer pipe opening portion 21 (proximal opening portion) of the end portion that is positioned on an outer side (opposite side on the center side of the winding) of the winding.

The outer pipe opening portion 21 is provided with a holder hub 25. The holder hub 25 is a pipe body into which the outer pipe opening portion 21 is inserted on one end side of the holder hub, and a strain relief 73 provided on the distal side of the hub portion 71 of the guiding catheter 70 is inserted the other end side thereof, and the holder hub holds the strain relief 73. It is possible to reliably maintain a state in which the guiding catheter 70 is connected to the outer pipe body 20 by the holder hub 25. Note that, in a case where the outer pipe opening portion 21 holds the strain relief 73 through processing or the like, the holder hub 25 may not be provided in the outer pipe opening portion 21.

The inner pipe body 30 has a spiral shape as a whole, with a tube that extends by a predetermined length and is wound on the center side of the winding of the outer pipe body 20. The inner pipe body 30 holds the inner catheter 80 so as to store and carry the catheter with the inner catheter 80 inserted through an inner pipe opening portion 31 (proximal opening portion) of an end portion that is positioned on the center side of the winding. The winding direction (clockwise direction in FIG. 1) of the inner pipe body 30 from the inner pipe opening portion 31 is an opposite direction to the winding direction (counterclockwise direction in FIG. 1) of the outer pipe body 20 from the outer pipe opening portion 21. The portion between the outer pipe opening portion 21 and the inner pipe opening portion 31 functions as a grasp portion 11 such that the operator grasps the portion. The grasp portion 11 is provided in the vicinity of the outer pipe opening portion 21 and the inner pipe opening portion 31.

The inner pipe opening portion 31 is provided with a holder hub 35. The holder hub 35 is a pipe body with one end side inserted into the inner pipe opening portion 31. In addition, the inner catheter 80 is inserted into the holder hub 35 on the other end side. At this time, a strain relief 83 provided on the distal side of the inner catheter is inserted into a lumen of the holder hub 35, or the hub portion 81 of the inner catheter 80 is fixed on an outer front surface of the holder hub 35. In this manner, the position of the inner catheter 80 is maintained. Therefore, it is possible to reliably maintain a state in which the inner catheter 80 is connected to the inner pipe body 30 through the holder hub 35. Note that, in a case where the inner pipe opening portion 31 can hold the strain relief 83 or the hub portion 81 through processing or the like, the holder hub 35 may not be provided in the inner pipe opening portion 31.

It is preferable that the outer pipe opening portion 21 and the inner pipe opening portion 31 are separated in a circumferential direction such that the grasp portion 11 is provided therebetween. For example, a separation angle α is set to 0° at a position at which the outer pipe opening portion 21 and the inner pipe opening portion 31 are coincident in the circumferential direction. In a case where the clockwise side in FIG. 1 is set to plus, and the counterclockwise side is set to minus, it is preferable that the outer pipe opening portion 21 is positioned in a range of 0° to +90°. Here, the separation angle α is an angle formed at an intersection point between a straight line from the outer pipe opening portion 21 to the center of the winding of the outer pipe body 20 and a straight line from the inner pipe opening portion 31 to the center of the winding of the inner pipe body 30.

There is no particular limitation on a material of the outer pipe body 20 and the inner pipe body 30 and it is possible to apply polyethylene, polypropylene, ethylene propylene copolymer, a polyolefin such as ethylene-vinyl acetate copolymer, polyvinyl chloride, polystyrene, polyamide, or polyimide.

Figure 2:
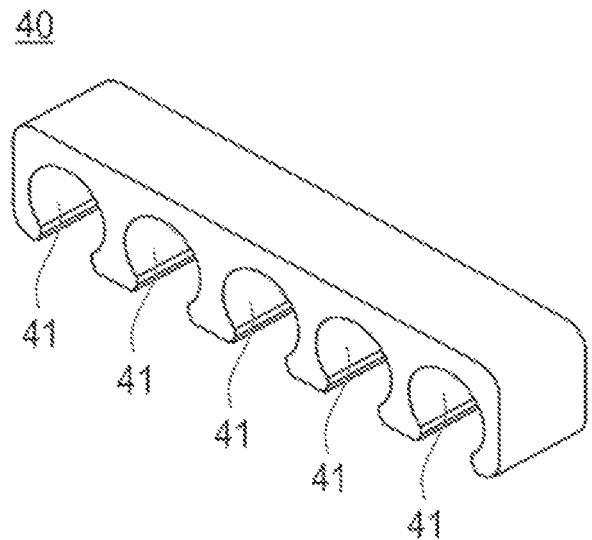
FIG. 2 is a perspective view of a connection member.

As illustrated in FIGS. 1 and 2, the several connection members 40 are provided in the circumferential direction of the outer pipe body 20 and the inner pipe body 30 and are fixed in a state in which adjacent tubes are arranged side by side from each other, and the outer pipe body 20 and the inner pipe body 30 are connected. The connection member 40 is provided with recessed portions 41 into which the outer pipe body 20 or the inner pipe body 30 is accommodated and which are disposed side by side. The outer pipe body 20 or the inner pipe body 30 is inserted into the recessed portion 41 and is connected, and thereby the spiral shape of the outer pipe body 20 and the inner pipe body 30 is maintained. In other words, the connection member 40 exhibits, as one member, both of a function of maintaining a winding state of the outer pipe body 20 and the inner pipe body 30 and a function of connecting the outer pipe body 20 and the inner pipe body 30. There is no particular limitation on a material of the connection member 40 and it is possible to apply polyethylene, polypropylene, a polyolefin such as ethylene propylene copolymer, polyvinyl chloride, polystyrene, polyamide, polycarbonate, various types of resin material such as acrylic resin, or the like.

Figure 3:
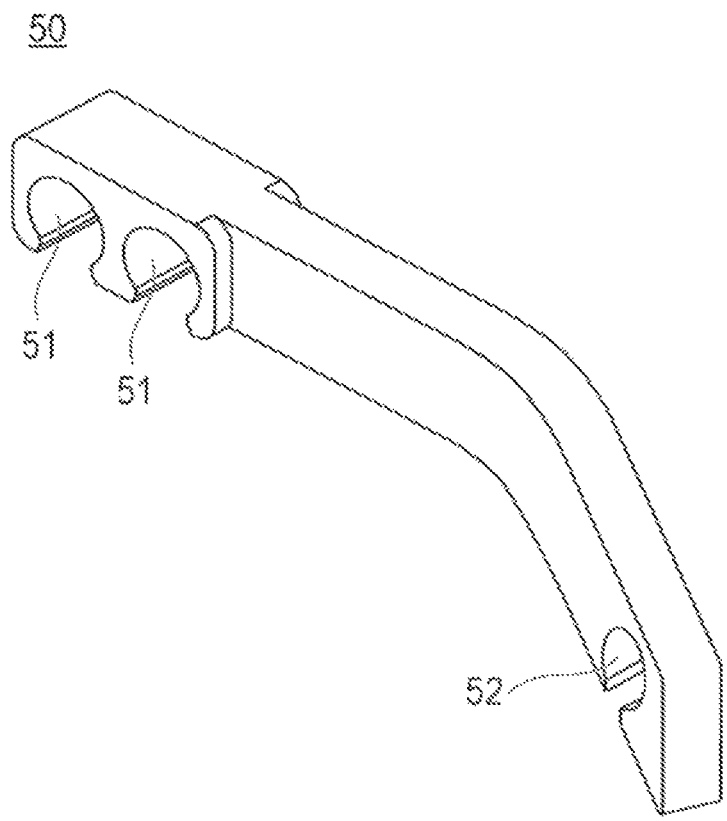
FIG. 3 is a perspective view of a holding member.
Figure 4:
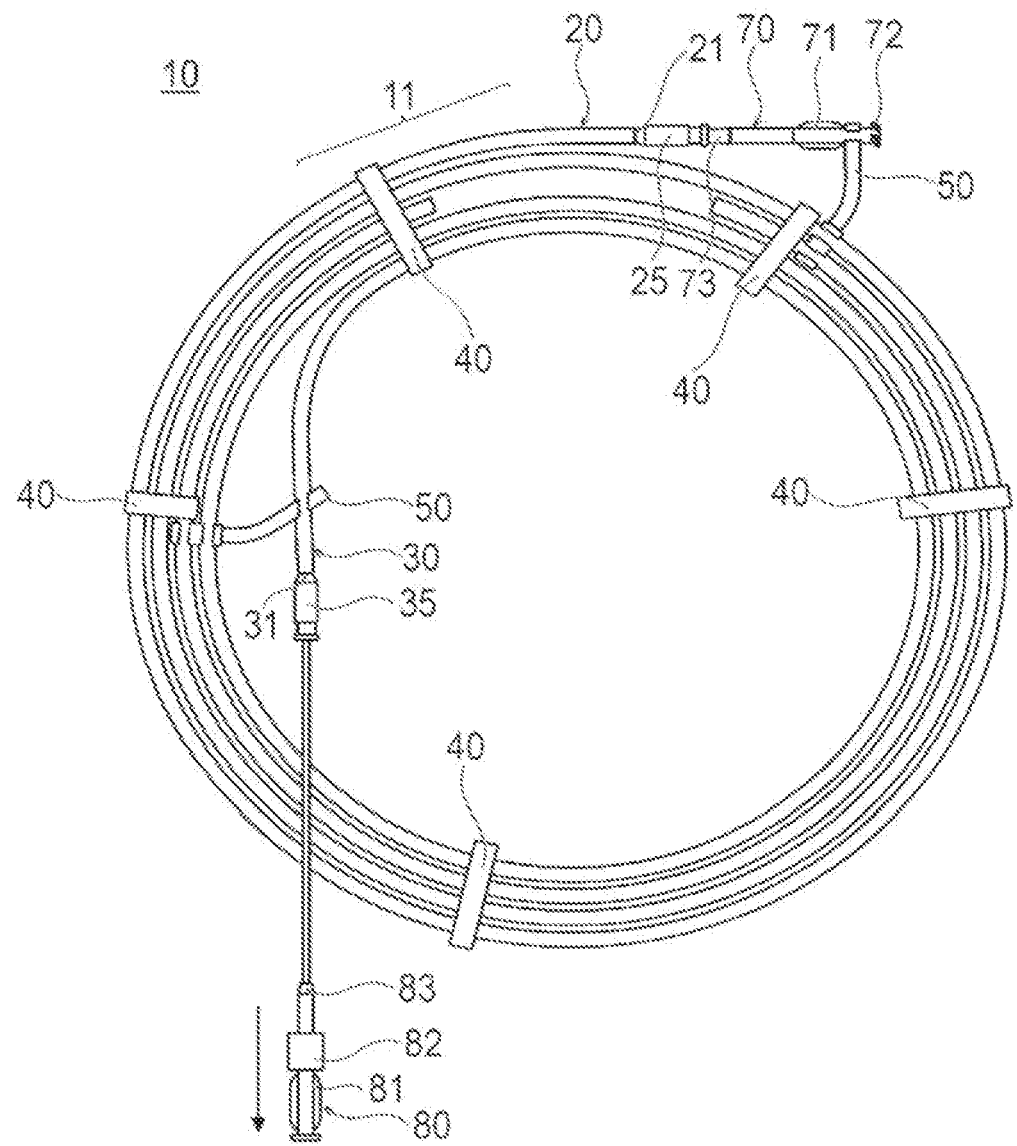
FIG. 4 is a plan view illustrating a state in which an inner catheter is pulled out from the storage case according to the first embodiment.
Figure 5:
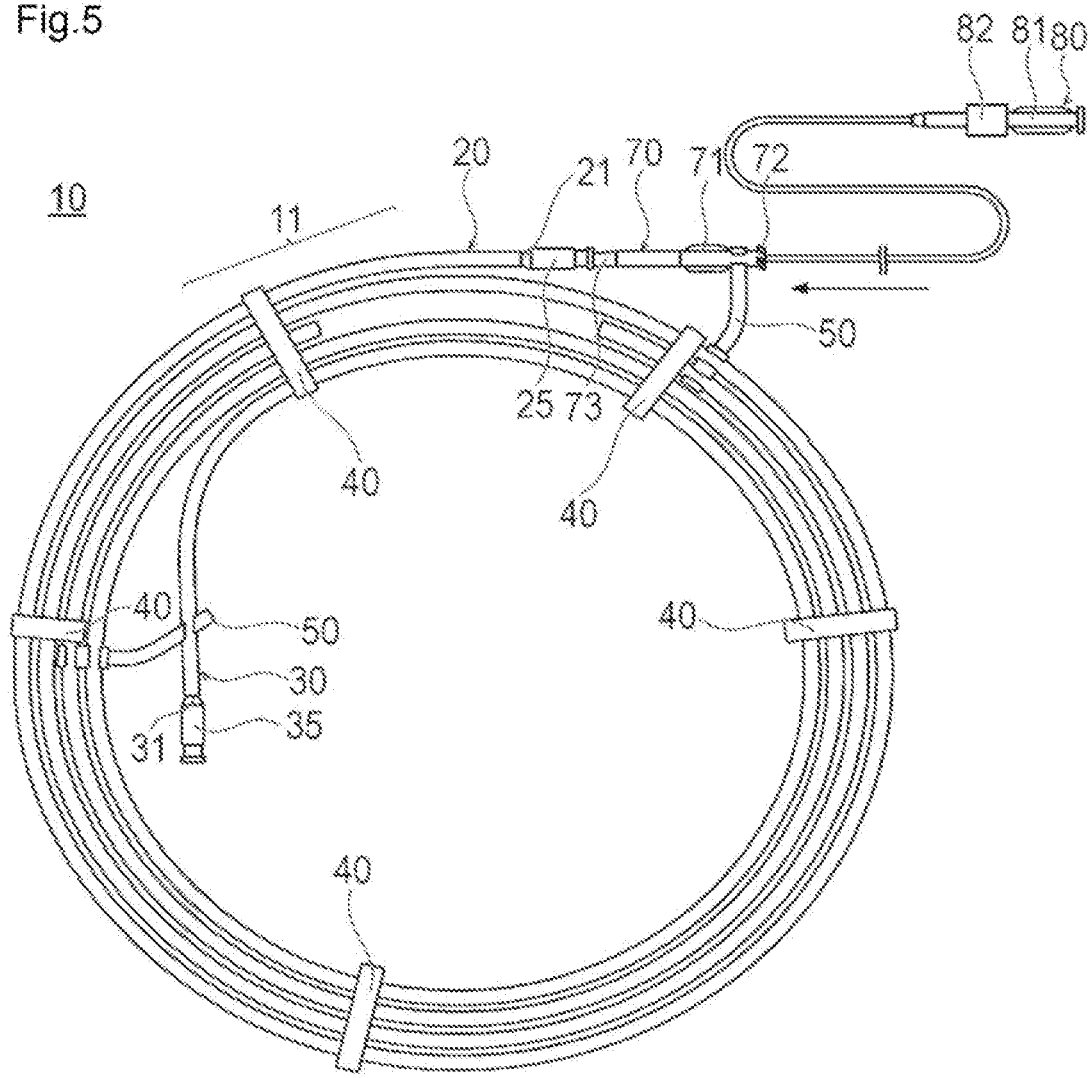
FIG. 5 is a plan view illustrating a state in which the inner catheter is inserted into a guiding catheter accommodated in the storage case according to the first embodiment.
Figure 6:
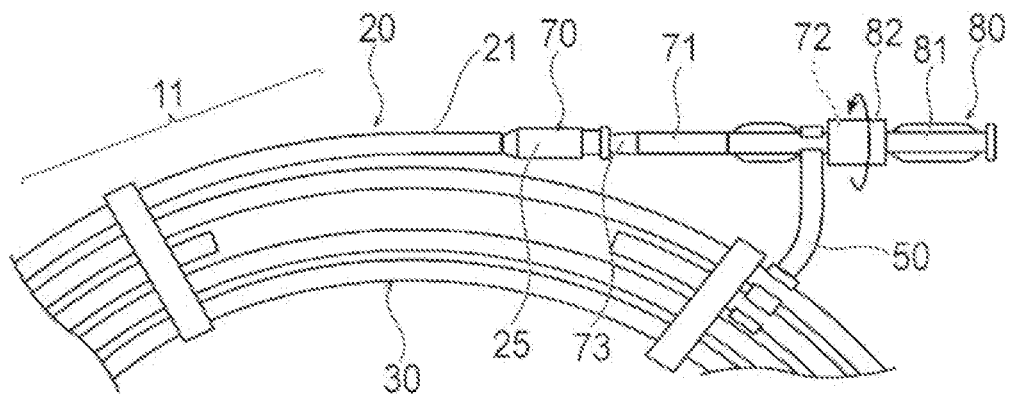
FIG. 6 is a plan view illustrating a state in which the inner catheter is connected to the guiding catheter accommodated in the storage case according to the first embodiment.
Figure 7:
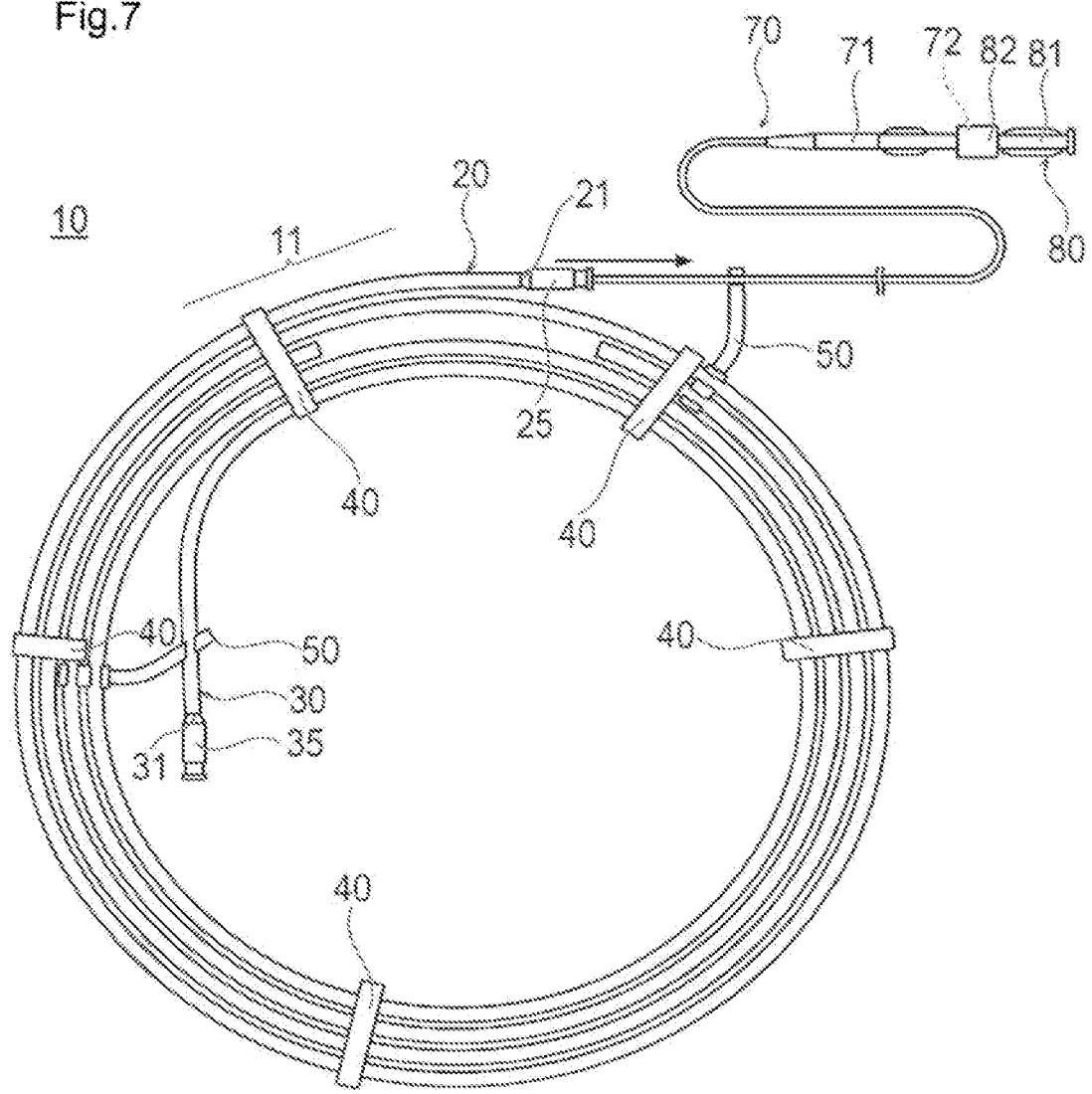
FIG. 7 is a plan view illustrating a state in which the guiding catheter and the inner catheter are pulled out from the storage case according to the first embodiment.

As illustrated in FIGS. 1 and 3, the holding member 50 is a member that holds the proximal portion of the guiding catheter 70, with one end connected to the outer pipe body 20, and the other end connected to the proximal portion of the guiding catheter 70. The holding member 50 is provided with first recessed portions 51 into which the outer pipe bodies 20 are accommodated and which are disposed side by side. The outer pipe bodies 20 are inserted into the first recessed portion 51 and are connected, and thereby the holding member is connected to the outer pipe body 20. Further, the holding member 50 is provided with second recessed portions 52 on a side opposite to the end portion in which the first recessed portion 51 is formed, the proximal portion of the guiding catheter 70 is inserted into and is connected to the second recessed portion 52, and thereby it is possible to hold the proximal portion of the guiding catheter 70. For example, the proximal portion of the guiding catheter 70 is a portion of the hub portion 71 or between the hub portion 71 and a locking thread 72. In addition, the holding member 50 is also used as a member that holds the end portion of the inner pipe body 30 on the center side of the winding.

As illustrated in FIG. 1, the package case 60 holds the catheters inside in a state in which the whole catheters are sterilized, with the guiding catheter 70 and the inner catheter 80 accommodated in the outer pipe body 20 and the inner pipe body 30 which are maintained to have the shape by the connection member 40. The package case 60 is formed to have a rectangular shape; however, there is no particular limitation on the shape. In general, the package case 60 is packaged with secondary package case with a box (not illustrated) so as to be stored and carried.

Figure 34:
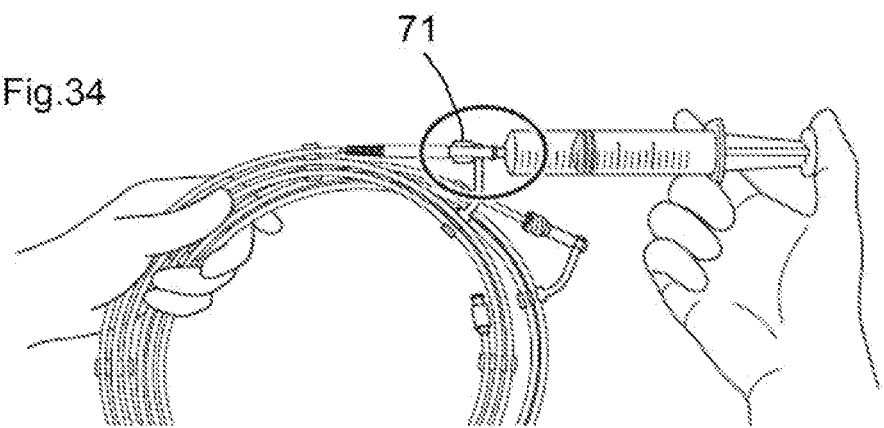
FIG. 34 is a perspective view illustrating a first step in a method of taking out the guiding catheter and the inner catheter from the storage case according to the first embodiment.
Figure 35:
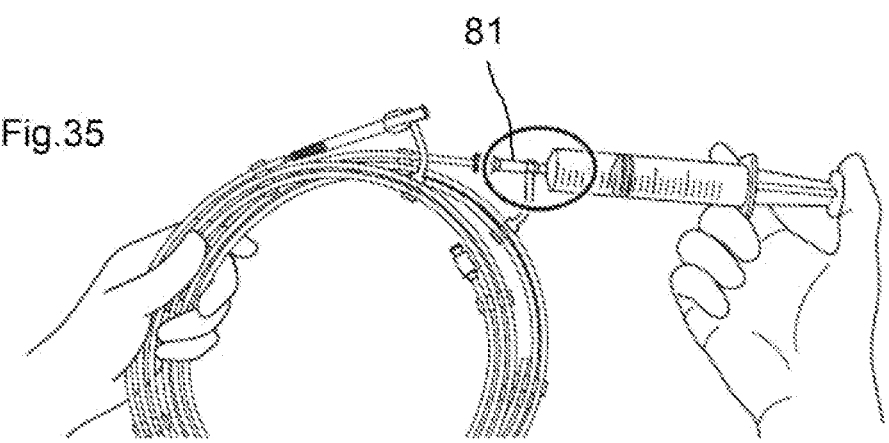
FIG. 35 is a perspective view illustrating a second step in the method of taking out the guiding catheter and the inner catheter from the storage case according to the first embodiment.
Figure 36:
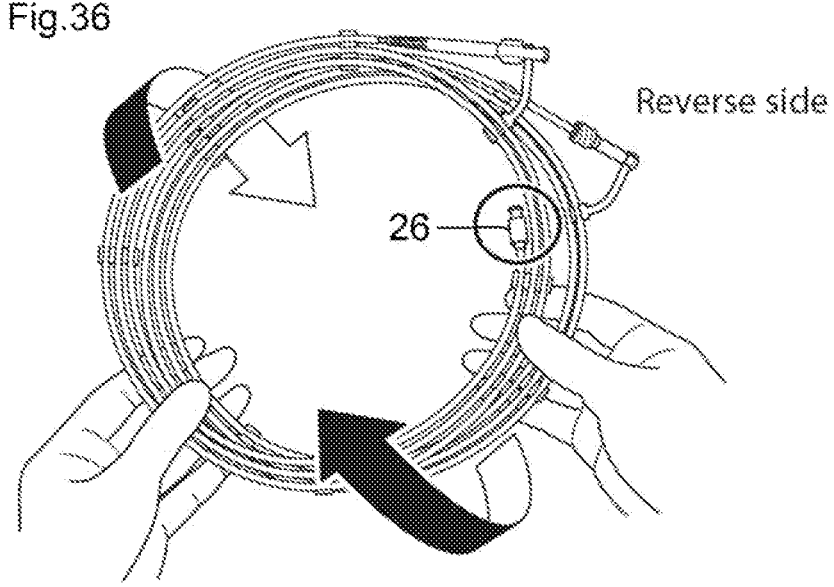
FIG. 36 is a perspective view illustrating a third step in the method of taking out the guiding catheter and the inner catheter from the storage case according to the first embodiment.
Figure 37:
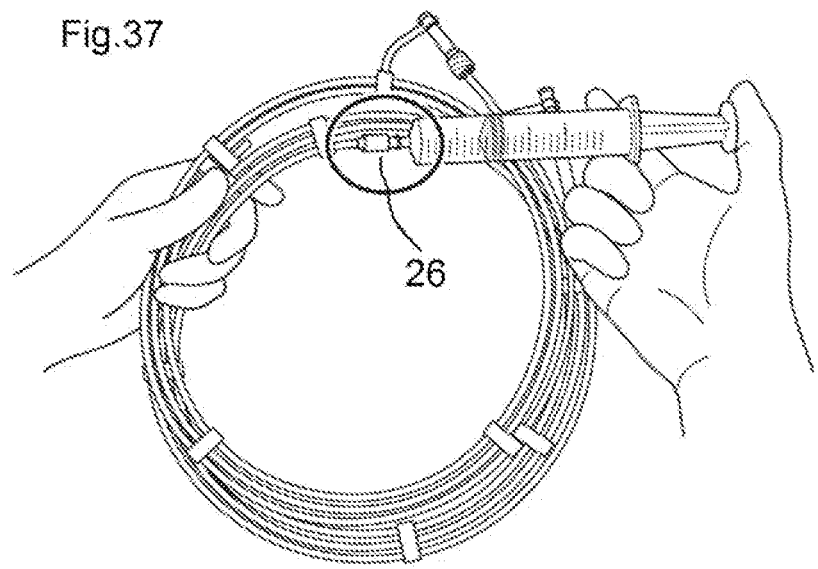
FIG. 37 is a perspective view illustrating a fourth step in the method of taking out the guiding catheter and the inner catheter from the storage case according to the first embodiment.
Figure 40:
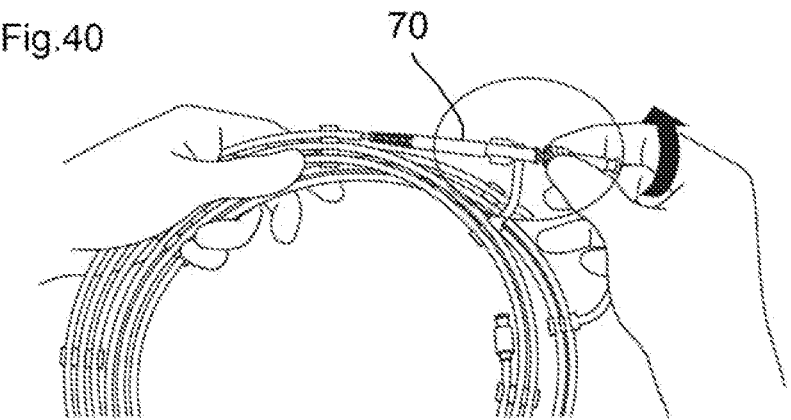
FIG. 40 is a perspective view illustrating a seventh step in the method of taking out the guiding catheter and the inner catheter from the storage case according to the first embodiment.
Figure 41:
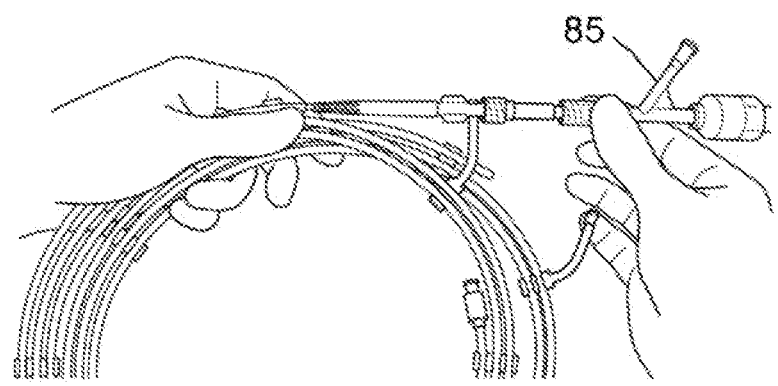
FIG. 41 is a perspective view illustrating an eighth step in the method of taking out the guiding catheter and the inner catheter from the storage case according to the first embodiment.

Next, a method of taking out the guiding catheter 70 and the inner catheter 80 from the storage case 10 according to the first embodiment will be described. First, the package case 60 is taken out from a box (not illustrated), the package case 60 is broken, the storage case in which the outer pipe body 20 and the inner pipe body 30 which accommodate the guiding catheter 70 and the inner catheter 80 are connected with the connection member is taken out. Next, a syringe is inserted into the hub portion 71 of the guiding catheter 70 as illustrated in FIG. 34, a heparinized physiological salt solution is injected, and priming of the inside of the guiding catheter 70 is performed. Next, a syringe is inserted into the hub portion 81 of the inner catheter 80 as illustrated in FIG. 35, a heparinized physiological salt solution is injected, and priming of the inside of the inner catheter 80 is performed. Next, a syringe is inserted into the holder hub 26 provided on a side opposite to an insertion portion of the first pipe body into which a catheter hub is inserted, the first pipe body accommodating the guiding catheter with the holder inside out as illustrated in FIGS. 36 and 37, a heparinized physiological salt solution is injected, and priming of an outer surface of the guiding catheter is performed. Next, the grasp portion 11 is grasped with one hand, and, as illustrated in FIG. 38, the inner catheter 80 is pulled out from the inner pipe body 30 with the other hand. Next, the pulled-out inner catheter 80 is inserted into the proximal opening portion of the guiding catheter 70 as illustrated in FIG. 39. Next, as illustrated in FIG. 40, the locking rotation portion 82 of the inner catheter 80 is caused to rotate and to be connected to a locking projection portion 72 of the guiding catheter 70. In this manner, the guiding catheter 70 and the pulled-out inner catheter 80 are in an assembled state. A hemostatic instrument such as a Y connector 85 is attached as illustrated in FIG. 41 as necessary. The guiding catheter 70 which is in a state where the inner catheter 80 is assembled, can then be pulled out from the outer pipe body 20 with the hand that pulls out the inner catheter 80. In this manner, the guiding catheter 70 and the pulled-out inner catheter 80 are in a state in which the catheters are taken out from the storage case 10. In the case of the priming, when the holder is inside out, a hand position is changed, a wrist is rotated, and then priming may be performed with one hand.

As described above, the storage case 10 according to the first embodiment is for accommodating a plurality of medical elongated bodies that are assembled when used. The storage case 10 includes the outer pipe body 20 and the inner pipe body 30 that are wound to form a ring-like shape and are connected to each other in order to accommodate both of the guiding catheter 70 (medical elongated body) and the inner catheter 80 (medical elongated body), and the connection member 40 that connects the outer pipe body 20 and the inner pipe body 30. Therefore, in the storage case 10, it is possible to collectively accommodate the guiding catheter 70 and the inner catheter 80, which are assembled when used, are collectively accommodated in one package case 60, and thus there is no need to individually package the guiding catheter 70 and the inner catheter 80. Hence, according to the storage case 10 according to the first embodiment, it is possible to reduce costs, time and effort required for the opening of the package is reduced such that the workability improves, and the waste is reduced such that it is possible to reduce the environmental impact, compared to a case where the guiding catheter 70 and the inner catheter 80 are individually packaged.

In addition, since the outer pipe body 20 and the inner pipe body 30 are connected by the connection member 40 and are accommodated in the package case 60, it is possible to reduce a shift of the outer pipe body 20 and the inner pipe body 30 in the package case 60, and it is possible to reduce necessity for individually taking out or a possibility that one catheter falls down.

In addition, since the outer pipe body 20 and the inner pipe body 30 are not integrally formed on both sides of one pipe body, but are formed as separate members, it is possible to reduce collision between a distal portion of the guiding catheter 70, which is accommodated in the outer pipe body 20, and a distal portion of the inner catheter 80, which is disposed in the inner pipe body 30.

In addition, since the outer pipe body 20 and the inner pipe body 30 are connected by the connection member 40 prepared as a separate member, the outer pipe body 20 and the inner pipe body 30 are connected by the connection member 40, and thereby it is possible to easily manufacture the storage case 10, and it is possible to separately use the outer pipe body 20 and the inner pipe body 30 after taken out from the package case 60 as necessary. In order to separately use the outer pipe body 20 and the inner pipe body 30, it is preferable that a first connection member that enables the winding state of the outer pipe body 20 and the inner pipe body 30 to be maintained after the separation and a second connection member that connects the outer pipe body 20 and the inner pipe body 30 are provided.

In addition, since the winding direction from the outer pipe opening portion 21 of the outer pipe body 20 from which the guiding catheter 70 is pulled out is a direction opposite to the winding direction from the inner pipe opening portion 31 of the inner pipe body 30, the grasp portion 11 between the outer pipe opening portion 21 and the inner pipe opening portion 31 is grasped, and thereby it is possible to easily insert the inner catheter 80 into the guiding catheter 70 that is accommodated in the outer pipe body 20 without changing the grasped position after the inner catheter 80 is pulled out from the inner pipe body 30. Thus, the operability improves. In particular, at the separation angle α of 0° to +90°, it is possible to easily and smoothly insert the inner catheter 80 into the guiding catheter 70 that is accommodated in the outer pipe body 20 after the inner catheter 80 is pulled out from the inner pipe body 30, with the grasped state of the grasp portion 11 maintained. Thus, the operability improves.

In addition, one of the pipe body is the outer pipe body 20 and the other of the pipe body is the inner pipe body 30 that is positioned on the center side of the winding of the outer pipe body 20, the medical elongated body accommodated in the outer pipe body 20 is the guiding catheter 70, and the medical elongated body accommodated in the inner pipe body 30 is the inner catheter 80 that is inserted into the guiding catheter 70. Therefore, it is possible to store, in the outer pipe body 20, the guiding catheter 70, which is thin to be easily bent, in a state in which the guiding catheter has a large curvature radius to the greatest extent, in order to provide a wide space inside to the largest extent.

In addition, since the storage case 10 of the embodiment has the package case 60 that collectively accommodates the outer pipe body 20 and the inner pipe body 30 which are connected to each other, it is possible to reduce the costs without the separate packaging of both the guiding catheter 70 and the inner catheter 80, time and effort required for the opening of the package is reduced such that the workability improves, and the waste is reduced such that it is possible to reduce the environmental impact.

Figure 8:
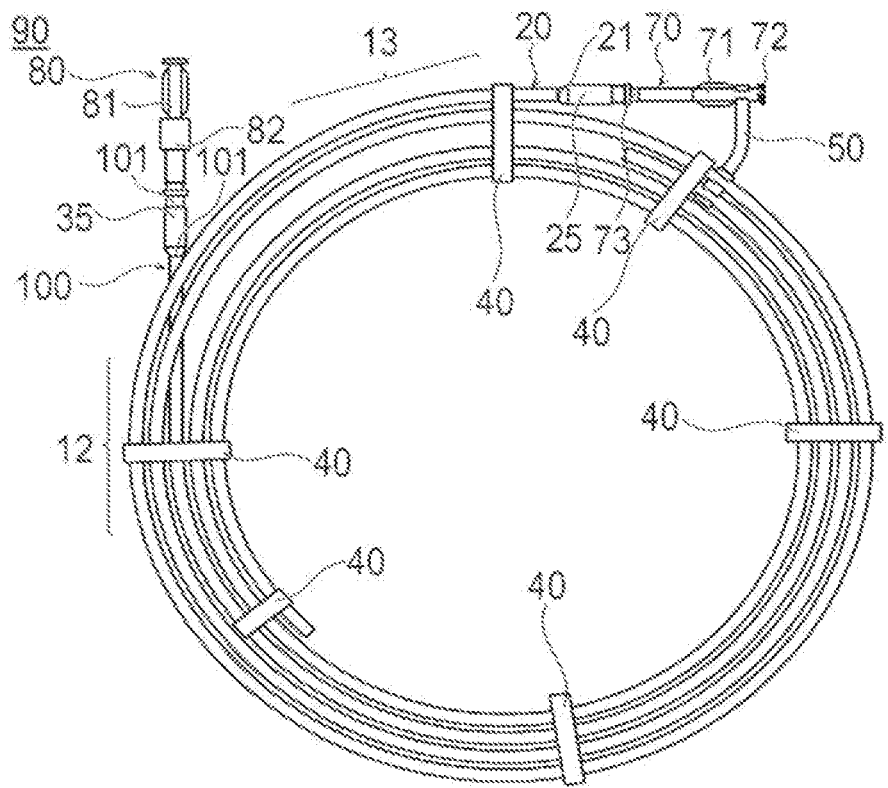
FIG. 8 is a plan view illustrating a storage case according to a second embodiment.

As illustrated in FIG. 8, a storage case 90 according to a second embodiment differs from that of the first embodiment in that the winding direction of an inner pipe body 100 is common to the outer pipe body 20. Note that the same reference signs are assigned to the same portions common to those of the first embodiment, and thus the description thereof is omitted.

The inner pipe body 100 of the storage case 90 according to the second embodiment has a spiral shape as a whole, with a tube that extends by a predetermined length and is wound on the center side of the winding of the outer pipe body 20. The inner pipe body 100 holds the inner catheter 80 so as to store and carry the catheter, with the inner catheter 80 inserted through an inner pipe opening portion 101 (proximal opening portion) of an end portion that is positioned on the outer side of the winding. The winding direction (counterclockwise direction in FIG. 8) of the inner pipe body 100 from the inner pipe opening portion 101 is the same direction as the winding direction of the outer pipe body 20 from the outer pipe opening portion 21. The inner pipe opening portion 101 of the inner pipe body 100 is separated from the outer pipe opening portion 21 of the outer pipe body 20. A portion in the vicinity of the winding direction of the inner pipe body 100 from the inner pipe opening portion 101 functions as a first grasp portion 12 that is grasped by the operator, and a portion in the vicinity of the winding direction of the outer pipe body 20 from the outer pipe opening portion 21 functions as a second grasp portion 13 that is grasped next by the operator.

Next, a method of taking out the guiding catheter 70 and the inner catheter 80 from the storage case 90 according to the second embodiment will be described. First, the package case 60 is taken out from the box, the package case 60 is broken, and the outer pipe body 20 and the inner pipe body 100 which accommodate the guiding catheter 70 and the inner catheter 80 are removed. Next, a syringe (not illustrated) is inserted into the hub portion 71 of the guiding catheter 70, and the physiological salt solution is injected such that the priming is performed on the inside of the guiding catheter 70. Next, a syringe (not illustrated) is inserted into the hub portion 81 of the inner catheter 80, and the physiological salt solution is injected such that the priming is performed on the inside of the inner catheter 80.

Figure 9:
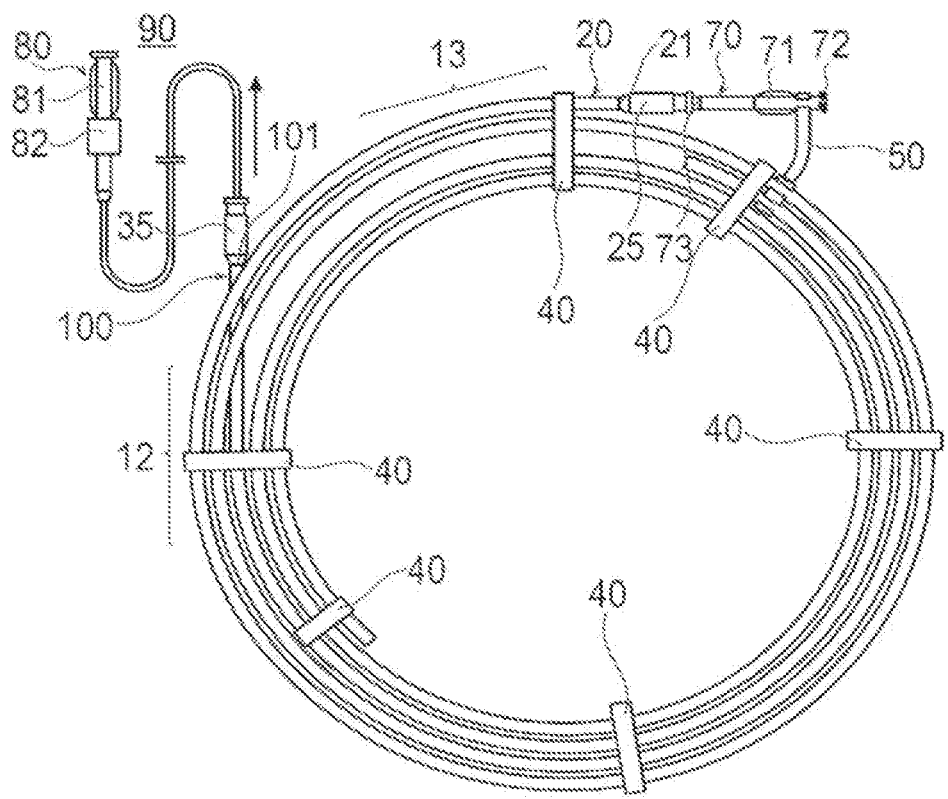
FIG. 9 is a plan view illustrating a state in which an inner catheter is pulled out from the storage case according to the second embodiment.
Figure 10:
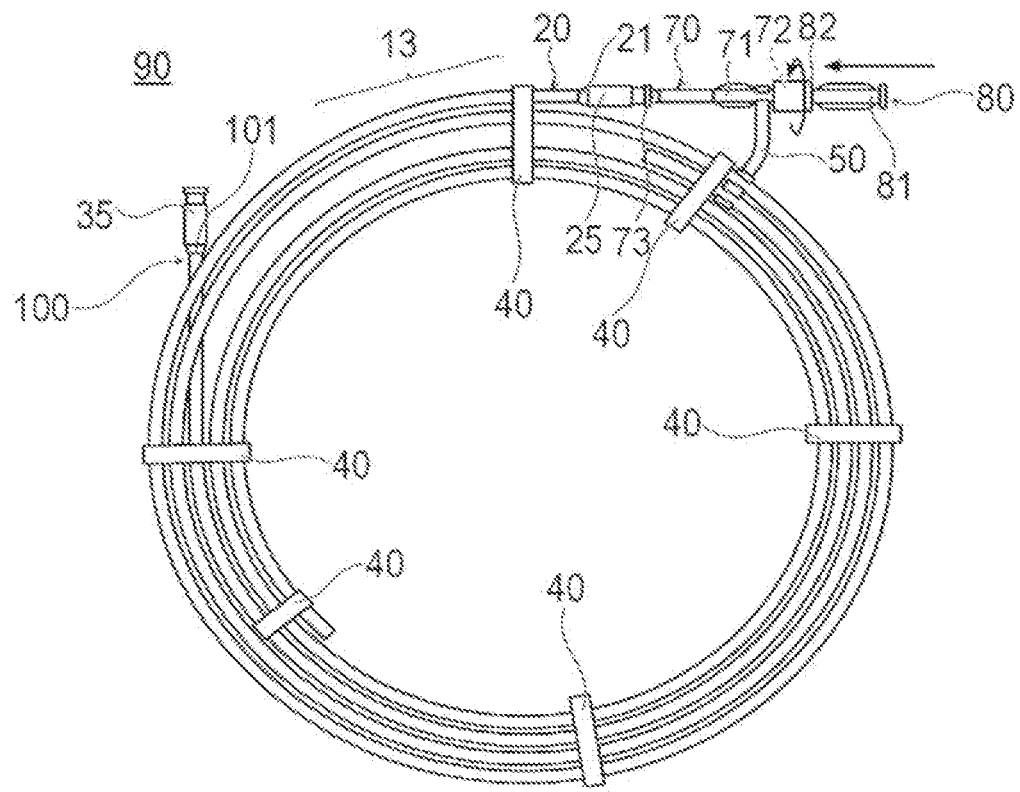
FIG. 10 is a plan view illustrating a state in which the inner catheter is inserted into and is connected to a guiding catheter accommodated in the storage case according to a second embodiment.
Figure 11:
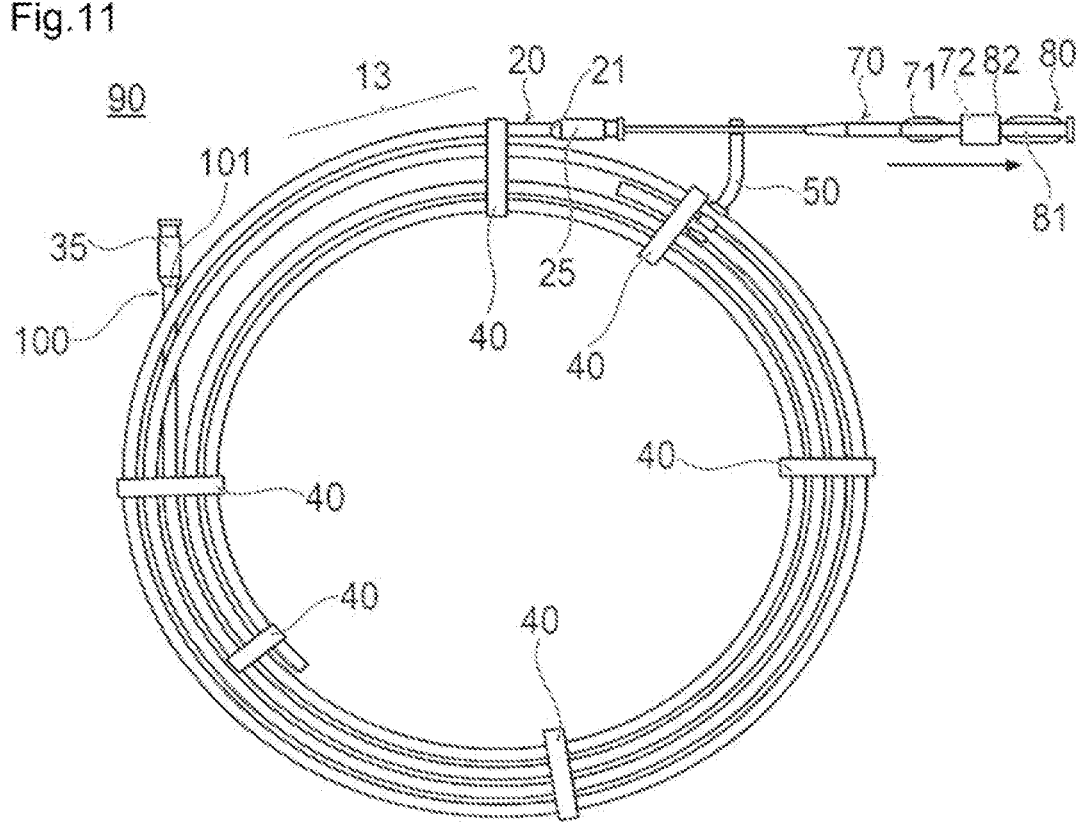
FIG. 11 is a plan view illustrating a state in which the guiding catheter and the inner catheter are pulled out from the storage case according to the second embodiment.

Next, the first grasp portion 12 is grasped with one hand, and, as illustrated in FIG. 9, the inner catheter 80 is pulled out from the inner pipe body 100 with the other hand. Next, the hand that holds the first grasp portion 12 moves to the second grasp portion 13 and grasps the second grasp portion 13, and the pulled-out inner catheter 80 is inserted into the proximal opening portion of the guiding catheter 70 with the other hand. Next, as illustrated in FIG. 10, the locking rotation portion 82 of the inner catheter 80 is caused to rotate and to be connected to the locking thread 72 of the guiding catheter 70. In this manner, the guiding catheter 70 and the inner catheter 80 are in an assembled state. Then, as illustrated in FIG. 11, the guiding catheter 70 which is in an assembled state with the inner catheter 80, is pulled out from the outer pipe body 20 with the hand that pulls out the inner catheter 80. In this manner, the guiding catheter 70 and the inner catheter 80 enter a state in which the catheters are taken out from the storage case 90.

As described above, in the storage case 90 according to the second embodiment, the winding direction of the inner pipe body 100 from the inner pipe opening portion 101 is the same direction as the winding direction of the outer pipe body 20 from the outer pipe opening portion 21, and thus the inner pipe opening portion 101 is separated from the outer pipe opening portion 21 in the winding direction. Therefore, the first grasp portion 12 in the vicinity of the inner pipe opening portion 101 of the inner pipe body 100 is grasped and the inner catheter 80 is pulled out. Then, the grasped position is changed to the second grasp portion 13 such that it is possible to insert and connect the inner catheter 80 into the guiding catheter 70.

Figure 12:
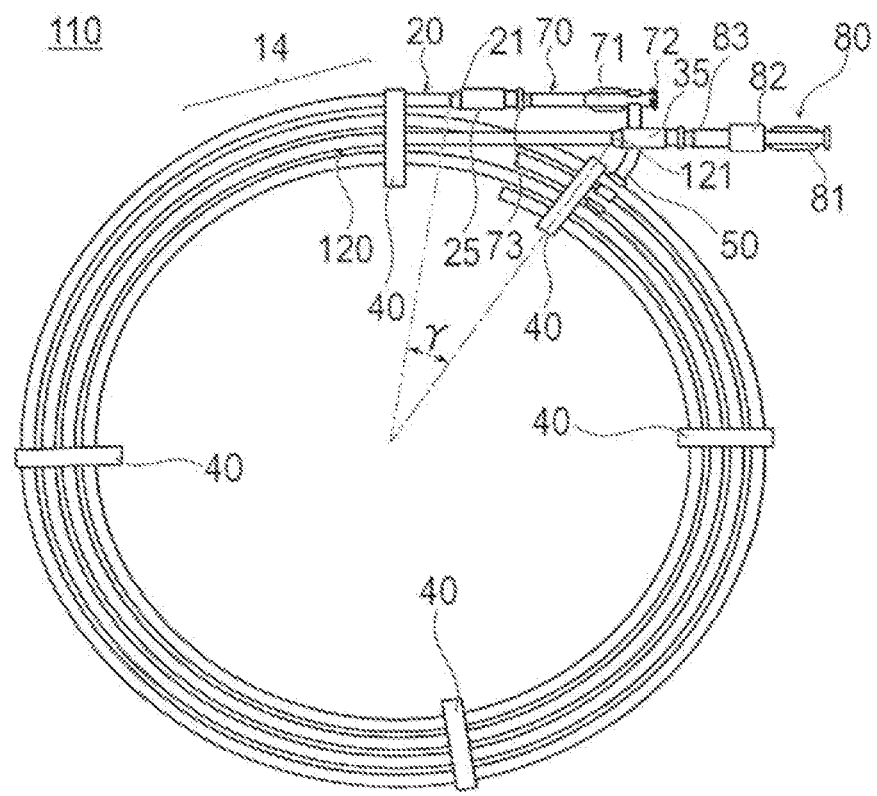
FIG. 12 is a plan view illustrating a storage case according to a third embodiment.

As illustrated in FIG. 12, a storage case 110 according to a third embodiment is the same as that of the first embodiment in that the winding direction of an inner pipe body 120 is the same as the winding direction of the outer pipe body 20, and the storage case differs from that of the first embodiment in that the outer pipe opening portion 21 of the outer pipe body 20 is close to an inner pipe opening portion 121 of the inner pipe body 120. Note that the same reference signs are assigned to the same portions common to those of the first embodiment, and thus the description thereof is omitted.

The inner pipe body 120 of the storage case 110 according to the third embodiment has a spiral shape as a whole, with a tube that extends by a predetermined length and is wound on the center side of the winding of the outer pipe body 20. The inner pipe body 120 holds the inner catheter 80 so as to store and carry the catheter, with the inner catheter 80 inserted through the inner pipe opening portion 121 of an end portion that is positioned on the outer side of the winding. The winding direction (counterclockwise direction in FIG. 12) of the inner pipe body 120 from the inner pipe opening portion 121 is the same direction as the winding direction of the outer pipe body 20 from the outer pipe opening portion 21. The inner pipe opening portion 121 of the inner pipe body 120 is close to the outer pipe opening portion 21 of the outer pipe body 20. For example, a separation angle γ in the winding direction between the inner pipe opening portion 121 and the outer pipe opening portion 21 is set to 0° at a position at which the outer pipe opening portion 21 and the inner pipe opening portion 121 are coincident in the circumferential direction. In a case where the clockwise side in FIG. 1 is set to plus, and the counterclockwise side is set to minus, it is preferable that the outer pipe opening portion 21 is positioned in a range of −45° to +45°. Here, the separation angle γ is an angle formed at an intersection point between a straight line from the outer opening portion 21 to the center of the winding of the outer pipe body 20 and a straight line from the inner pipe opening portion 121 to the center of the winding of the inner pipe body 120. In addition, a portion in the vicinity of the winding direction of the inner pipe body 120 from the inner pipe opening portion 121 and of the outer pipe body 20 from the outer pipe opening portion 21 functions as a grasp portion 14 that is grasped by the operator.

Figure 13:
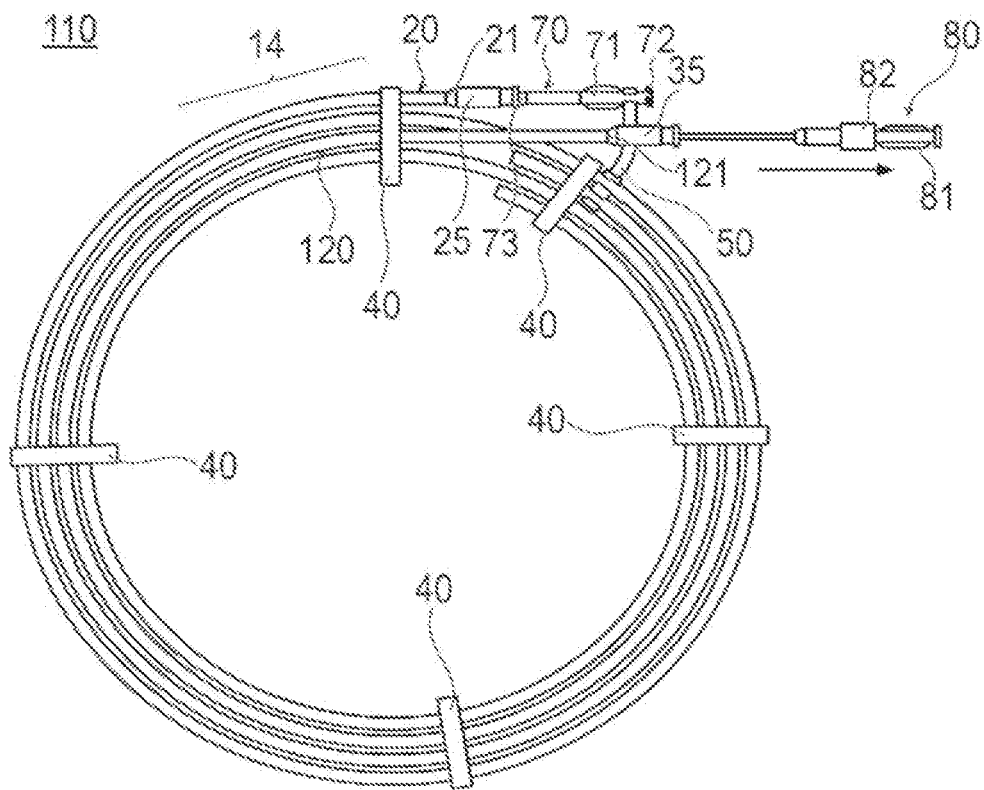
FIG. 13 is a plan view illustrating a state in which an inner catheter is pulled out from the storage case according to the third embodiment.
Figure 14:
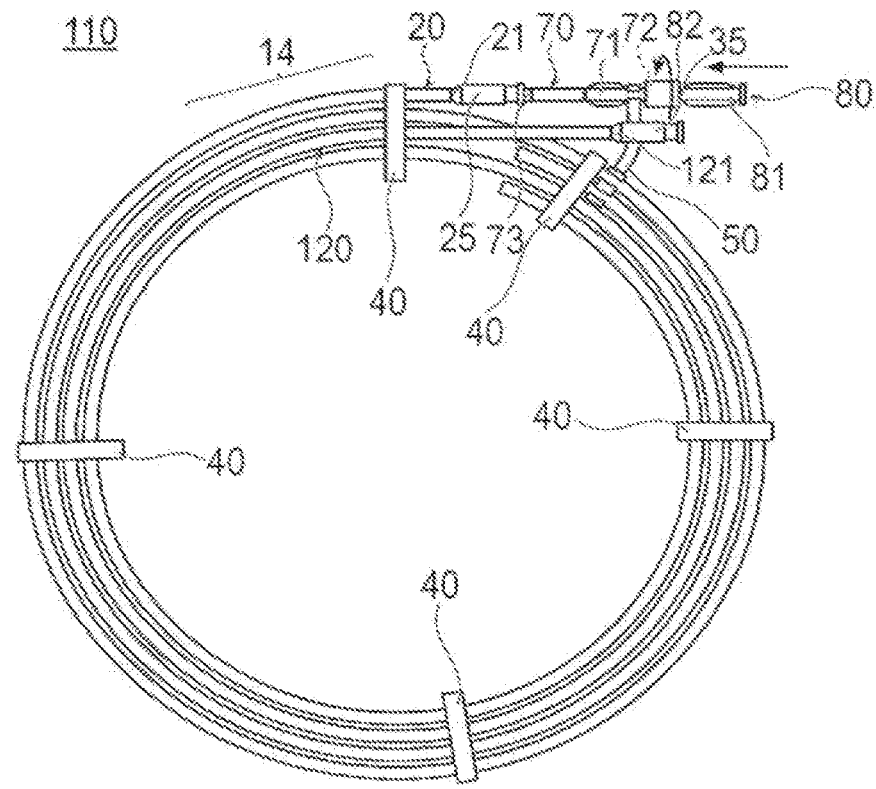
FIG. 14 is a plan view illustrating a state in which the inner catheter is inserted into and is connected to the guiding catheter accommodated in the storage case according to the third embodiment.
Figure 15:
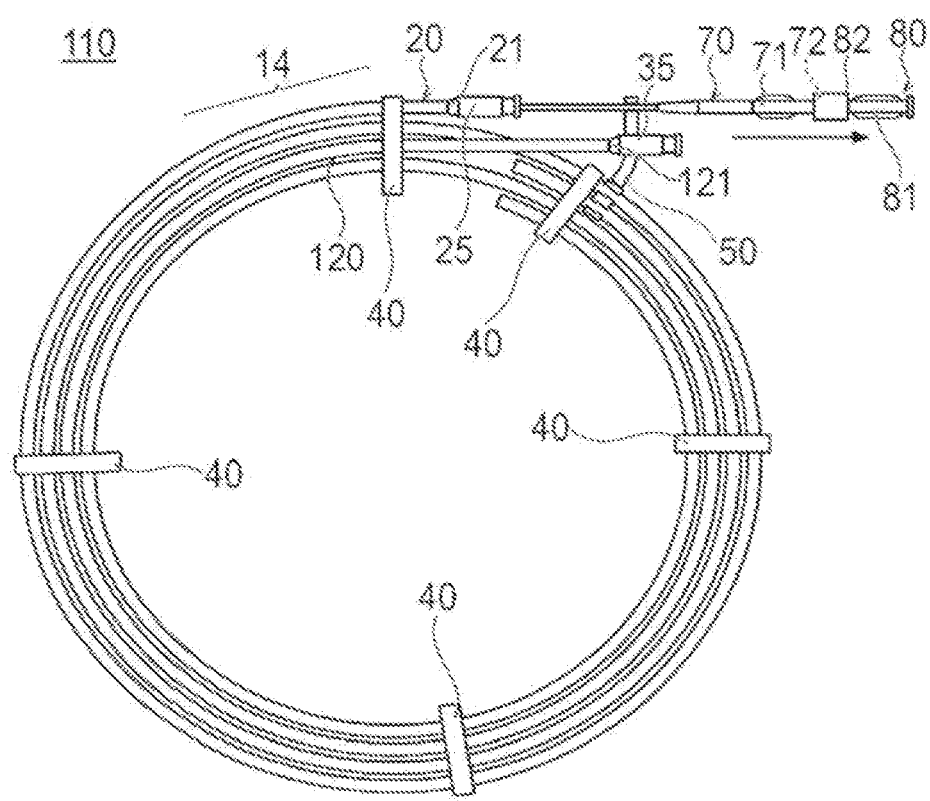
FIG. 15 is a plan view illustrating a state in which the guiding catheter and the inner catheter are pulled out from the storage case according to the third embodiment.

Next, a method of taking out the guiding catheter 70 and the inner catheter 80 from the storage case 110 according to the third embodiment will be described. First, the package case 60 is taken out from the box, the package case 60 is broken, and the outer pipe body 20 and the inner pipe body 120 which accommodate the guiding catheter 70 and the inner catheter 80 are removed. Next, a syringe (not illustrated) is inserted into the hub portion 71 of the guiding catheter 70, and the physiological salt solution is injected such that the priming is performed on the inside of the guiding catheter 70. Next, a syringe (not illustrated) is inserted into the hub portion 81 of the inner catheter 80, and the physiological salt solution is injected such that the priming is performed on the inside of the inner catheter 80. Next, the grasp portion 14 is grasped with one hand, and, as illustrated in FIG. 13, the inner catheter 80 is pulled out from the inner pipe body 120 with the other hand. Next, as illustrated in FIG. 14, a state in which the grasp portion 14 is grasped with one hand is maintained, and the pulled-out inner catheter 80 is inserted into the proximal opening portion of the guiding catheter 70 with the other hand. Then, the locking rotation portion 82 of the inner catheter 80 is caused to rotate and to be connected to the locking thread 72 of the guiding catheter 70. In this manner, the guiding catheter 70 and the inner catheter 80 are in an assembled state. Then, as illustrated in FIG. 15, with the grasp portion 14 grasped with one hand, the guiding catheter 70 which is in an assembled state with the inner catheter 80, is pulled out from the outer pipe body 20 with the other hand that pulls out the inner catheter 80. In this manner, the guiding catheter 70 and the inner catheter 80 are in a state of being taken out from the storage case 110.

As described above, in the storage case 110 according to the third embodiment, the winding direction of the inner pipe body 120 from the inner pipe opening portion 121 is the same direction as the winding direction of the outer pipe body 20 from the outer pipe opening portion 21, and thus the inner pipe opening portion 121 is close to the outer pipe opening portion 21 in the winding direction. Therefore, it is possible to easily insert the inner catheter 80 into the guiding catheter 70 that is accommodated in the outer pipe body 20 without changing the grasp position after the inner catheter 80 is pulled out from the inner pipe body 120. Thus, the operability improves. In particular, at the separation angle γ of −45° to +45°, it is possible to easily and smoothly insert the inner catheter 80 into the guiding catheter 70 that is accommodated in the outer pipe body 20 after the inner catheter 80 is pulled out from the inner pipe body 120 with the grasped state of the grasp portion 14 maintained. Thus, the operability improves.

Figure 16:
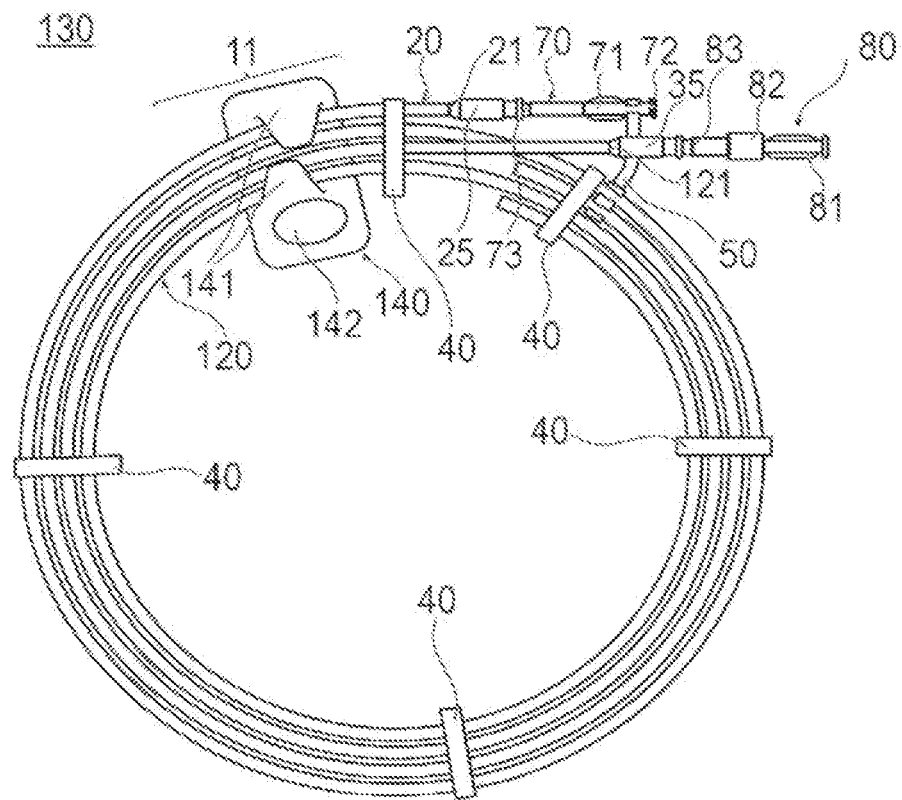
FIG. 16 is a plan view illustrating a storage case according to a fourth embodiment.

As illustrated in FIG. 16, a storage case 130 according to a fourth embodiment differs from that of the third embodiment only in that an assistive member 140 for assisting the grasp is added. Note that the same reference signs are assigned to the same portions common to those of the third embodiment, and thus the description thereof is omitted.

The assistive member 140 of the storage case 130 according to the fourth embodiment is formed of a single sheet-shaped member, and is provided with a pair of engagement portions 141 that is interposed between the grasp portions 14 of the outer pipe body 20 and the inner pipe body 120 and engages with the grasp portions 14. The engagement portion 141 is formed with a notch in the assistive member 140. In addition, the assistive member 140 is provided with an insertion hole 142, into which a thumb is inserted, at a position on the center side of the winding direction from the inner pipe body 120 in a state in which the outer pipe body 20 and the inner pipe body 120 are attached.

There is no particular limitation on a material of the assistive member 140 and it is possible to apply paper or a resin material such as polyethylene, polypropylene, ethylene propylene copolymer, a polyolefin such as ethylene-vinyl acetate copolymer, polyvinyl chloride, polystyrene, polyamide, or polyimide. Note that the assistive member 140 may not be the sheet-shaped member.

In a case where the guiding catheter 70 and the inner catheter 80 are taken out from the storage case 130 according to the fourth embodiment, not only the outer pipe body 20 and the inner pipe body 120 are grasped, but also the assistive member 140 is grasped with the thumb inserted into the insertion hole 142, when the grasp portion 11 is grasped. As described above, with the assistive member 140 present, it is possible to easily recognize the portion that is grasped and it is easy to perform grasping, and thus the operability improves.

Figure 17:
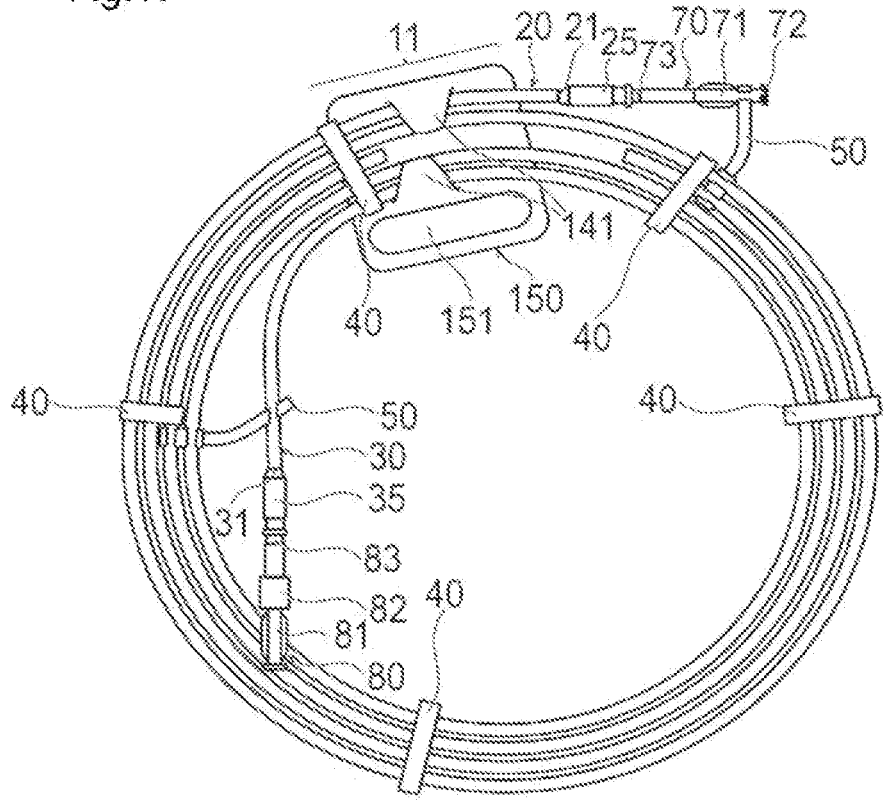
FIG. 17 is a plan view illustrating a modification example of the storage case according to the fourth embodiment.
Figure 18:
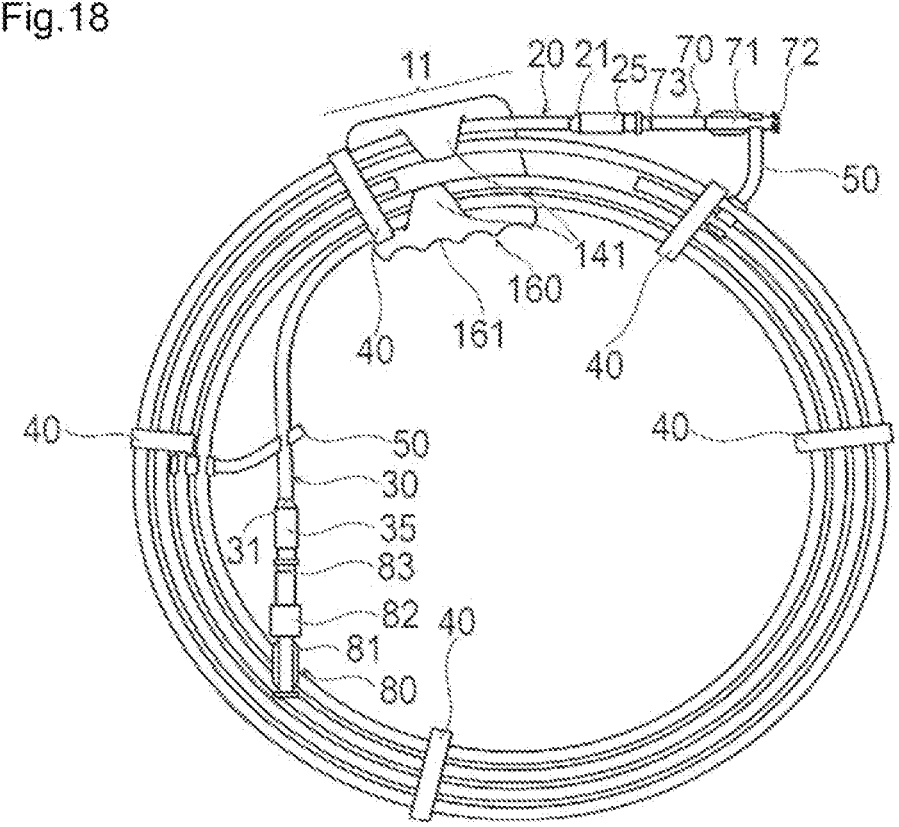
FIG. 18 is a plan view illustrating another modification example of the storage case according to the fourth embodiment.

Note that a modification example of the storage case 130 according to the fourth embodiment, as illustrated in FIG. 17, may include an insertion hole 151 of an assistive member 150 that has an elongated shape in one direction. In this manner, it is possible to collectively insert fingers other than the thumb into the insertion hole 151 so as to perform the grasp. In addition, the insertion hole of the assistive member is not formed on the center side of the winding of the outer pipe body 20 and the inner pipe body 30, and may be formed on the outer side. In addition, as another modification example illustrated in FIG. 18, a grip portion 161 having a shape that is easily gripped by fingers may be provided at an edge portion of an assistive member 160. In addition, a portion in which the assistive member is connected is not provided on the outer pipe body 20 and the inner pipe body 30, and may be provided on the connection member 40.

In addition, various types of information may be provided on the assistive member 140. The information includes a precautionary note that is referred to when the guiding catheter 70 and the inner catheter 80 are taken out from the storage case 130 or when the catheters are used.

Figure 19:
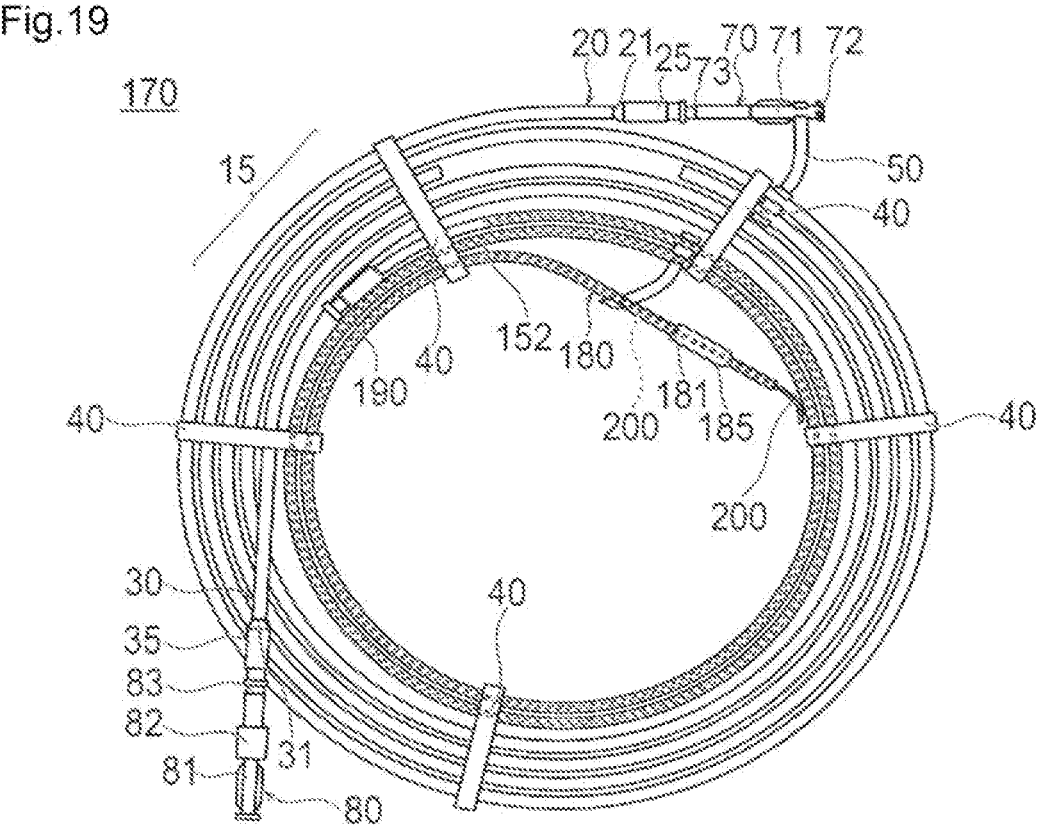
FIG. 19 is a plan view illustrating a storage case according to a fifth embodiment.

As illustrated in FIG. 19, a storage case 170 according to a fifth embodiment differs from that of the first embodiment in that a third pipe body 180 (pipe body) is added. Note that the same reference signs are assigned to the same portions common to those of the first embodiment, and thus the description thereof is omitted.

The storage case 170 according to the fifth embodiment includes the third pipe body 180, in which a tube extending by a predetermined length is wound on the center side of the winding of the inner pipe body 30. The outer pipe body 20, the inner pipe body 30, and the third pipe body 180 are connected by a connection member 210. The third pipe body 180 accommodates a guide wire 200 (medical elongated body) that can be pulled out from a third opening portion 181 (proximal opening portion) of an end portion that is positioned on the center side of the winding, and the third pipe body holds the guide wire 200 so as to store and carry the guide wire. For example, the guide wire 200 is used to guide the guiding catheter 70, which is in the assembled state with the inner catheter 80, into a body lumen. In addition, the winding direction (counterclockwise direction in FIG. 19) of the third pipe body 180 from the third opening portion 181 is the opposite direction to the winding direction of the inner pipe body 30 from the inner pipe opening portion 31, and is the same direction as the winding direction of the outer pipe body 20 from the outer pipe opening portion 21. The portion between the third opening portion 181 and the inner pipe opening portion 31 between the outer pipe opening portion 21 and the inner pipe opening portion 31 functions as a grasp portion 15 such that the operator grasps the portion. The grasp portion 15 is provided in the vicinity of all of the outer pipe opening portion 21, the inner pipe opening portion 31, and the third opening portion 181.

An inserter 185 is connected to the third opening portion 181 of the third pipe body 180, and a holder hub 190 is connected to an end portion on the opposite side to the third opening portion 181. The inserter 185 communicates with the lumen of the third pipe body 180 and is formed to have a tube shape with a diameter reduced toward a distal end. The inserter 185 protects the distal end of the guide wire 200 and guides the guide wire 200 when the guide wire is inserted into the catheter or the like.

The holder hub 190 communicates with the lumen of the third pipe body 180 such that a liquid such as a physiological salt solution or the like is injected from a syringe, with the syringe connected thereto, and thereby it is possible to guide the liquid into the lumen of the third pipe body 180.

There is no particular limitation on materials of the third pipe body 180, the inserter 185, and the holder hub 190, and, for example, it is possible to apply various types of resin materials such as polyethylene, polypropylene, a polyolefin such as ethylene propylene copolymer, polyvinyl chloride, polystyrene, polyamide, polycarbonate, or an acrylic-based resin. However, it is preferable that a relatively soft material is used so as to be elastically deformed.

Figure 20:
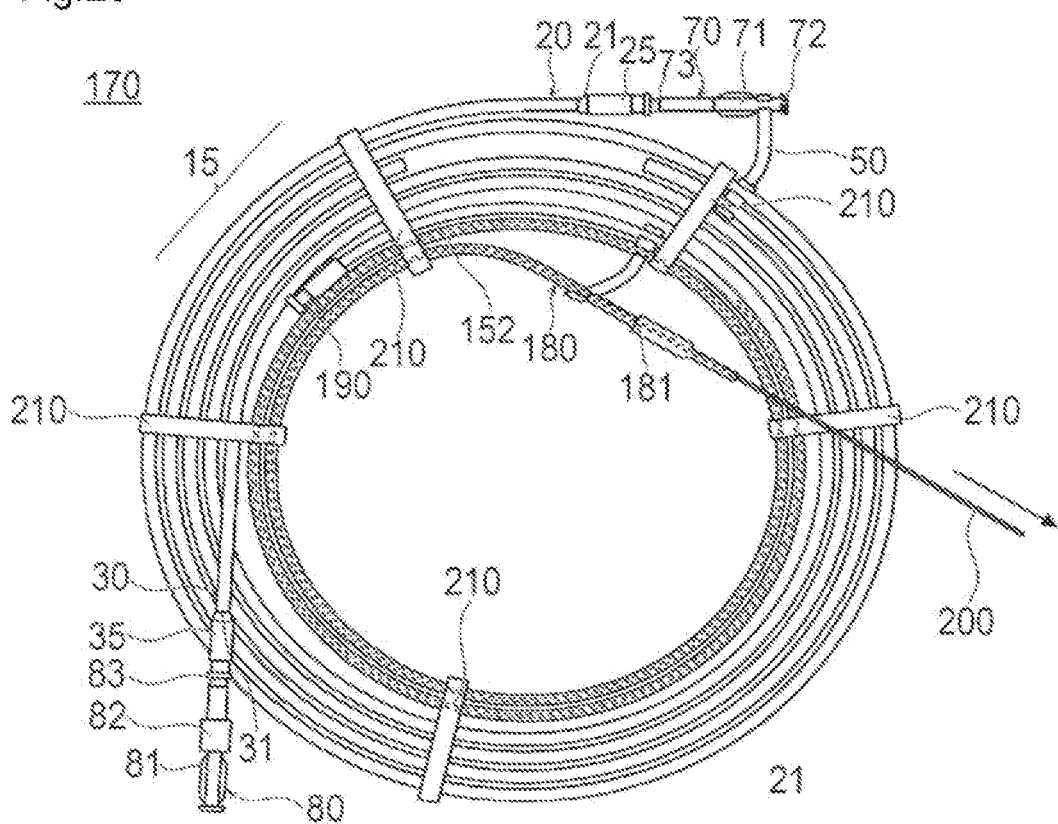
FIG. 20 is a plan view illustrating a state in which a guide wire is pulled out from the storage case according to the fifth embodiment.

Next, a method of taking out the guiding catheter 70 and the inner catheter 80 from the storage case 170 according to the fifth embodiment will be described. First, the package case 60 is taken out from the box, the package case 60 is broken, and the outer pipe body 20, the inner pipe body 30, and the third pipe body 180, which accommodate the guiding catheter 70, the inner catheter 80, and the guide wire 200, are taken out. Next, a syringe (not illustrated) is inserted into the holder hub 190, and the physiological salt solution is injected into the third pipe body 180. Next, the grasp portion 15 is grasped with one hand, the holder hub 190 is detached with the other hand, as illustrated in FIG. 20, such that the guide wire 200 is pulled out from the third pipe body 180 and the guide wire 200 enters a vat containing the physiological salt solution. Next, a state in which the grasp portion 15 is grasped with one hand is maintained, and, in the same procedure as that of the first embodiment, the inner catheter 80 is inserted into and is connected to the proximal opening portion of the guiding catheter 70 with the hand that has pulled out the guide wire 200. Then, the guiding catheter 70 and the inner catheter 80 are pulled out from the outer pipe body 20 in the assembled state of the catheters. In this manner, the guide wire 200, the guiding catheter 70, and the inner catheter 80 are in a state of being taken out from the storage case 170.

As described above, in the storage case 170 according to the fifth embodiment, since the outer pipe body 20, the inner pipe body 30, and the third pipe body 180, which accommodate the guide wire 200, the guiding catheter 70, and the inner catheter 80 which are assembled when used, are connected to each other, it is possible to collectively accommodate the catheters and the wire in one package case. Therefore, there is no need to individually package the guide wire 200, the guiding catheter 70, and the inner catheter 80. Hence, according to the storage case 170, it is possible to reduce costs, time and effort required for the opening of the package is reduced such that the workability improves, and the waste is reduced such that it is possible to reduce the environmental impact, compared to a case where the guide wire 200, the guiding catheter 70, and the inner catheter 80 are individually packaged.

In addition, the third pipe body 180, the inner pipe body 30, and the outer pipe body 20 are disposed to have the winding directions which are alternately opposite from the opening portion in an order in which the medical elongated bodies accommodated in the pipe bodies, respectively, are pulled out, and thus the grasp portion 15 is close to all of the outer pipe opening portion 21, the inner pipe opening portion 31, and the third opening portion 181. Therefore, in a pulling-out operation, it is easy to recognize the next operation without changing the portion that is grasped, and thus the operability improves. Note that the winding directions of the pipe bodies from the opening portions may not be alternately opposite in accordance with the pulling-out procedure of the medical elongated bodies accommodated in the pipe bodies, respectively. In addition, after the guiding catheter 70 and the inner catheter 80 are assembled to be pulled out, the guide wire 200 may be pulled out from the third pipe body 180.

Figure 21:
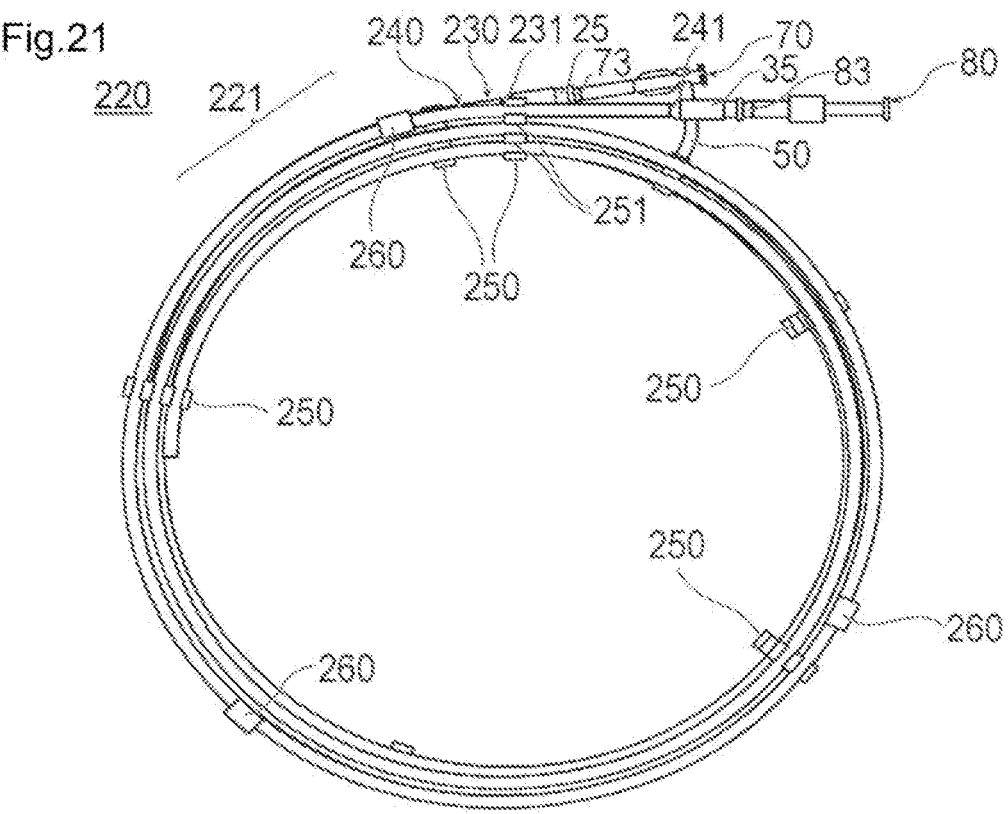
FIG. 21 is a plan view illustrating a storage case according to a sixth embodiment.
Figure 22:
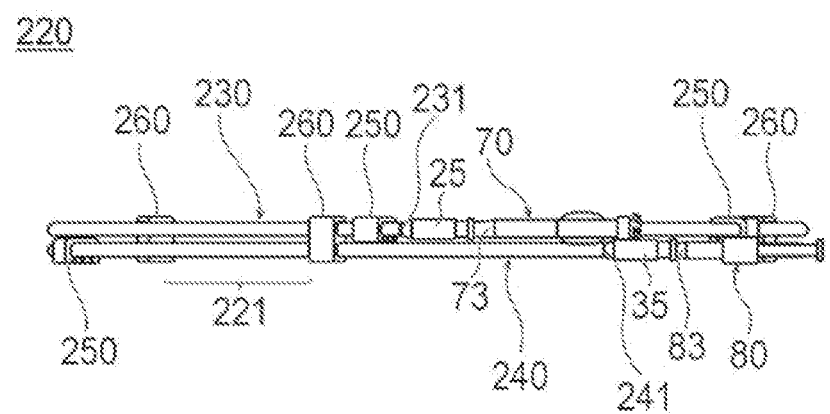
FIG. 22 is a side view illustrating the storage case according to the sixth embodiment.

As illustrated in FIGS. 21 and 22, a storage case 220 according to a sixth embodiment differs from the storage cases according to the first to fifth embodiments described above in that the medical elongated bodies are disposed side by side such that a first pipe body 230 and a second pipe body 240 overlap each other. Note that the same reference signs are assigned to the same portions common to those of the embodiments described above, and thus the description thereof is omitted.

The storage case 220 includes a first pipe body 230 (pipe body) that accommodates the guiding catheter 70, a second pipe body 240 (pipe body) that accommodates the inner catheter 80, a first connection member 250 for maintaining shapes of the first pipe body 230 and the second pipe body 240, a second connection member 260 (connection member)

for connecting the first pipe body 230 and the second pipe body 240, and a package case 60 that holds the pipe bodies and members inside in a sterilized state.

The first pipe body 230 has a spiral shape as a whole, with a tube that extends by predetermined length and is wound. The first pipe body 230 holds the guiding catheter 70 so as to store and carry the catheter with the guiding catheter 70 inserted through a first opening portion 231 (proximal opening portion) of the end portion that is positioned on an outer side (opposite side on the center side of the winding) of the winding.

The second pipe body 240 has a spiral shape as a whole, with a tube that extends to a predetermined length and is wound. The second pipe body 240 holds the inner catheter 80 so as to store and carry the catheter, with the inner catheter 80 inserted through a second opening portion 241 (proximal opening portion) of an end portion that is positioned on the outer side of the winding. A winding direction (counterclockwise direction in FIG. 20) of the second pipe body 240 from the second opening portion 241 is the same direction as the winding direction of the first pipe body 230 from the first opening portion 231. The maximum outer circumferential diameters of the winding of the first pipe body 230 and the second pipe body 240 are substantially equal to each other. The first pipe body 230 and the second pipe body 240 are disposed to overlap each other in a direction along the center axis of the winding. In other words, two planes on which the first pipe body 230 and the second pipe body 240 are wound are positioned to be substantially parallel to each other. The portion of the first opening portion 231 and the second opening portion 241 on the winding direction side functions as a grasp portion 221 such that the operator grasps the portion. The grasp portion 221 is provided in the vicinity of both of the first opening portion 231 and the second opening portion 241.

There is no particular limitation on materials of the first pipe body 230 and the second pipe body 240, and it is possible to apply polyethylene, polypropylene, ethylene propylene copolymer, a polyolefin such as ethylene-vinyl acetate copolymer, polyvinyl chloride, polystyrene, polyamide, or polyimide.

Several first connection members 250 are provided in the circumferential direction of the first pipe body 230 the second pipe body 240 and are fixed in a state in which adjacent tubes are arranged side by side from each other. The first connection member 250 is provided with recessed portions 251 into which the first pipe body 230 or the second pipe body 240 is accommodated and which are disposed side by side. The first pipe body 230 or the second pipe body 240 is pushed into the recessed portion 251 and is connected, and thereby the spiral shapes of the first pipe body 230 and the second pipe body 240 are maintained.

Figure 23:
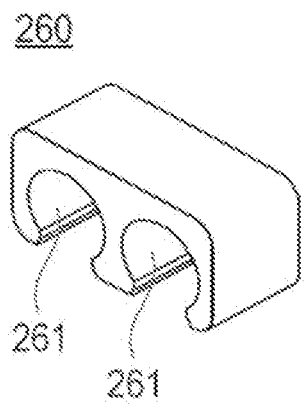
FIG. 23 is a perspective view illustrating a second connection member of the storage case according to the sixth embodiment.

Several second connection members 260 are provided in the circumferential direction (winding direction) of the first pipe body 230 and the second pipe body 240 and are fixed in a state in which the first pipe body 230 and the second pipe body 240 are disposed side by side. As illustrated in FIG. 23, the second connection member 260 is provided with recessed portions 261 into which the first pipe body 230 or the second pipe body 240 is accommodated and which are disposed side by side. The first pipe body 230 or the second pipe body 240 is inserted into the recessed portion 251 so as to be connected, and thereby the connection state between the first pipe body 230 and the second pipe body 240 is maintained.

There is no particular limitation on materials of the first connection member 250 and the second connection member 260 and it is possible to apply polyethylene, polypropylene, a polyolefin such as ethylene propylene copolymer, PVC, polystyrene, polyamide, polycarbonate, various types of resin material such as acrylic resin, or the like.

Figure 24:
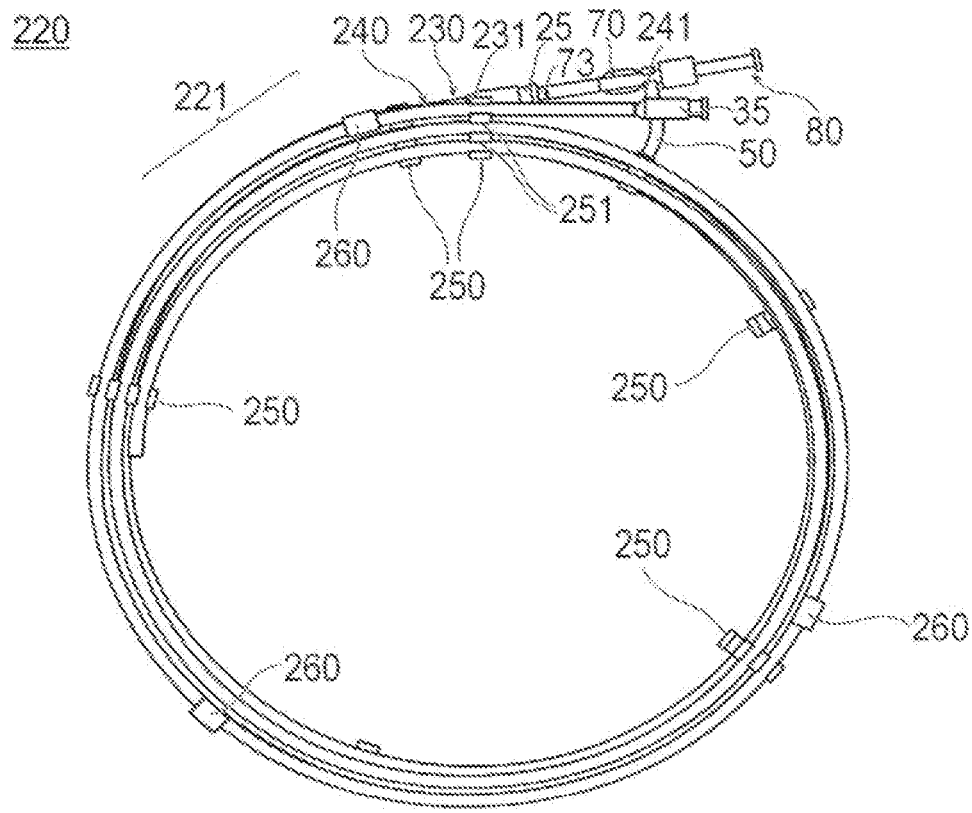
FIG. 24 is a plan view illustrating a state in which the inner catheter is inserted into and is connected to the guiding catheter accommodated in the storage case according to the sixth embodiment.
Figure 25:
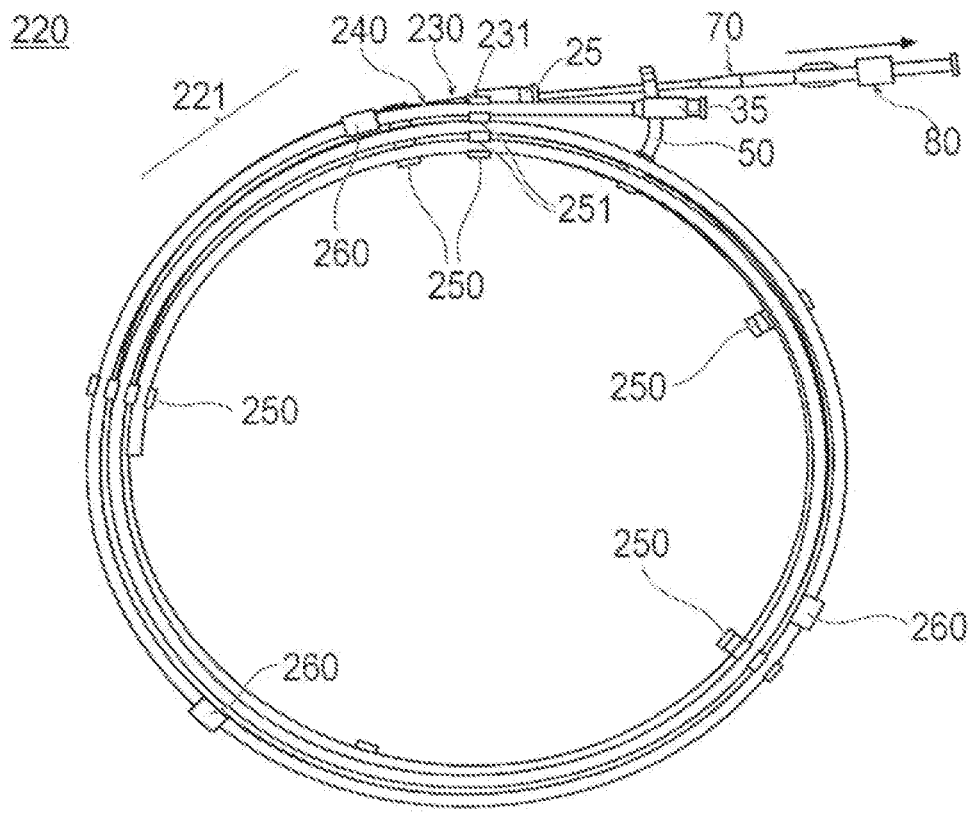
FIG. 25 is a plan view illustrating a state in which the guiding catheter and the inner catheter are pulled out from the storage case according to the sixth embodiment.

Next, a method of taking out the guiding catheter 70 and the inner catheter 80 from the storage case 220 according to the sixth embodiment will be described. First, the package case 60 is taken out from the box, the package case 60 is broken, and the first pipe body 230 and the second pipe body 240 which accommodate the guiding catheter 70 and the inner catheter 80 are taken out. Next, a syringe (not illustrated) is inserted into the hub portion 71 of the guiding catheter 70, and the physiological salt solution is injected such that the priming is performed on the inside of the guiding catheter 70. Next, a syringe (not illustrated) is inserted into the hub portion 81 of the inner catheter 80, and the physiological salt solution is injected such that the priming is performed on the inside of the inner catheter 80. Next, the grasp portion 221 is grasped with one hand and the inner catheter 80 is pulled out from the second pipe body 240 with the other hand. Next, a state in which the grasp portion 221 is grasped with one hand is maintained, and the pulled-out inner catheter 80 is inserted into the proximal opening portion of the guiding catheter 70 with the other hand. As illustrated in FIG. 24, the guiding catheter 70 and the inner catheter 80 are in the assembled state. Then, as illustrated in FIG. 25, with the grasp portion 221 grasped with one hand, the guiding catheter 70 which is in the assembled state with the inner catheter 80, is pulled out from the first pipe body 230 with the other hand that pulls out the inner catheter 80. In this manner, the guiding catheter 70 and the inner catheter 80 are in the state of being taken out from the storage case 220.

As described above, in the storage case 220 according to the sixth embodiment, since the first pipe body 230 and the second pipe body 240 are disposed to overlap each other in a direction along the center axis of the winding, it is possible to reduce the maximum outer circumferential diameters of the winding of the first pipe body 230 and the second pipe body 240 without disposing the first pipe body 230 and the second pipe body 240 on the same surface such that it is possible to perform storage in a compact space and a wide width is formed with the first pipe body 230 and the second pipe body 240 overlapping each other. Further, both of the first opening portion 231 and the second opening portion 241 are easily caused to be close to the grasp portion 221, the grasp is easily performed and the operability improves.

In addition, in the storage case 220 according to the sixth embodiment, since the second connection member 260 that connects the first pipe body 230 and the second pipe body 240 is separately provided from the first connection member 250 for maintaining the winding states of the first pipe body 230 and the second pipe body 240, it is possible to sufficiently reduce a shift of the first pipe body 230 and the second pipe body 240 in the package case 60. In addition, when the storage case 220 according to the sixth embodiment is taken out from the package case 60, it is possible to sufficiently reduce a concern that one of the pipe bodies will fall down.

Further, in the storage case 220 according to the sixth embodiment, since the second connection member 260 that connects the first pipe body 230 and the second pipe body 240 is separately provided from the first connection member 250 for maintaining the winding states of the first pipe body 230 and the second pipe body 240, it is possible to take out the guiding catheter 70 and the inner catheter 80 from the first pipe body 230 and the second pipe body 240 after the second connection member 260 is detached to be separated, with the winding states maintained by the first connection member 250, as necessary.

Figure 26:
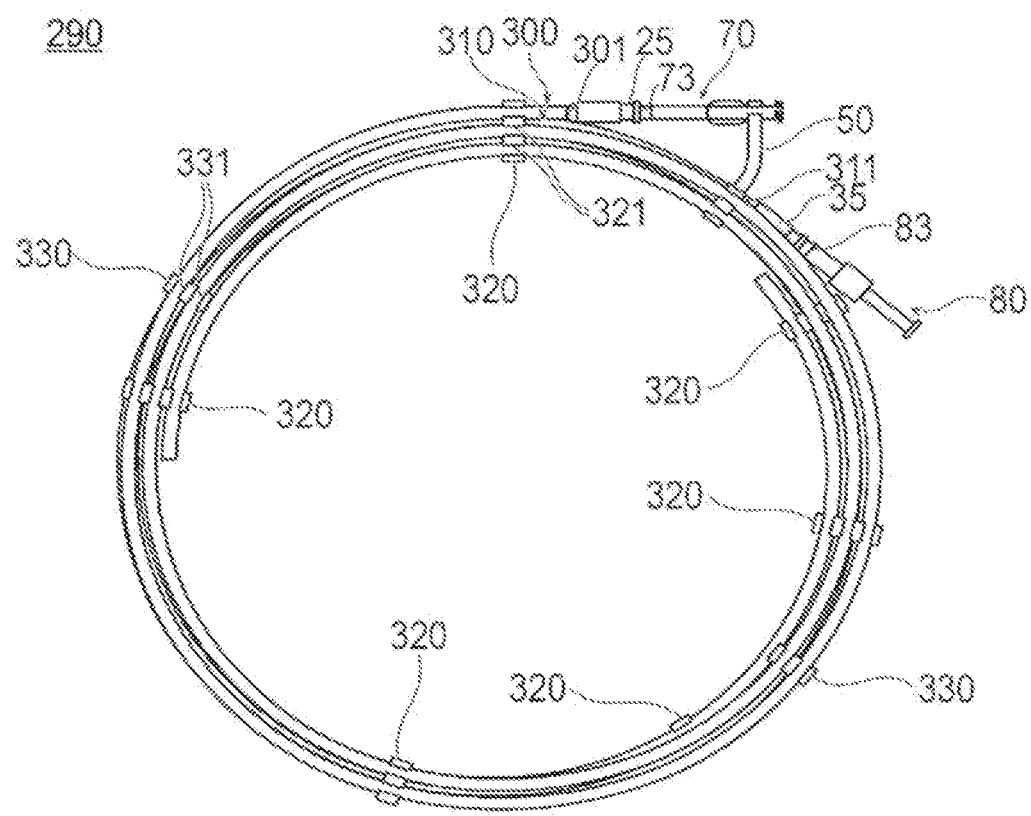
FIG. 26 is a plan view illustrating a storage case according to a seventh embodiment.

As illustrated in FIG. 26, a storage case 290 according to a seventh embodiment differs from the storage cases according to the first to sixth embodiments described above in that a structure that connects a first pipe body 300 and a second pipe body 310 that accommodate the medical elongated bodies is provided. Note that the same reference signs are assigned to the same portions common to those of the embodiments described above, and thus the description thereof is omitted.

The storage case 290 includes the first pipe body 300 (pipe body) that accommodates the guiding catheter 70, the second pipe body 310 (pipe body) that accommodates the inner catheter 80, a first connection member 320 (connection member) for maintaining shapes of the first pipe body 300 and the second pipe body 310, a second connection member 330 (connection member) that connects the first pipe body 300 and the second pipe body 310, and the package case 60 that holds the pipe bodies and members inside in the sterilized state.

The first pipe body 300 has a spiral shape as a whole, with a tube that extends by predetermined length and is wound. The first pipe body 300 holds the guiding catheter 70 so as to store and carry the catheter with the guiding catheter 70 inserted through a first opening portion 301 (proximal opening portion) of the end portion that is positioned on the outer side of (opposite side on the center side of the winding) of the winding.

The second pipe body 310 has a spiral shape as a whole, with a tube that extends to a predetermined length and is wound. The second pipe body 310 holds the inner catheter 80 so as to store and carry the catheter, with the inner catheter 80 inserted through a second opening portion 311 (proximal opening portion) of an end portion that is positioned on the outer side of the winding. A winding direction (counterclockwise direction in FIG. 26) of the second pipe body 310 from the second opening portion 311 is the same direction as the winding direction of the first pipe body 300 from the first opening portion 301. The maximum outer circumferential diameters of the winding of the first pipe body 300 and the second pipe body 310 are substantially equal to each other. The first pipe body 300 and the second pipe body 310 are disposed to overlap each other in a direction along the center axis of the winding. In other words, two planes on which the first pipe body 300 and the second pipe body 310 are wound are positioned to be substantially parallel to each other. There is no particular limitation on the materials of the first pipe body 300 and the second pipe body 310.

Figure 27A:
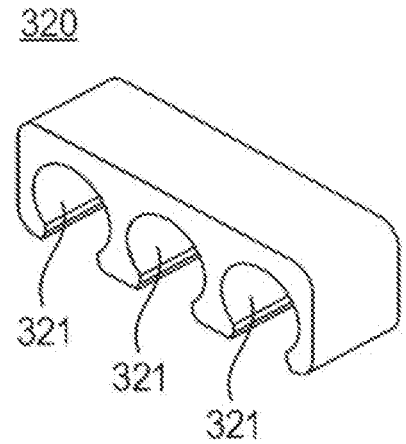
FIG. 27A is a perspective view illustrating a first connection member of the storage case according to the seventh embodiment.
Figure 27B:
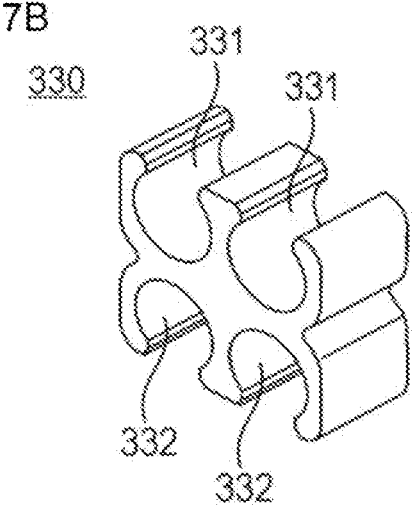
FIG. 27B is a perspective view illustrating a second connection member of the storage case according to the seventh embodiment.

As illustrated in FIGS. 26, 27A, and 27B, several first connection members 320 are provided in the circumferential direction of the first pipe body 300 and the second pipe body 310 and are fixed in a state in which adjacent tubes are arranged side by side from each other. The first connection member 320 is provided with a plurality of recessed portions 321 into which the first pipe body 300 or the second pipe body 310 is accommodated and which are disposed side by side. The first pipe body 300 or the second pipe body 310 is pushed into the recessed portion 321 and is connected, and thereby the spiral shapes of the first pipe body 300 and the second pipe body 310 are maintained. Note that there is no particular limitation on the number of recessed portions 321 in the single first connection member 320.

One or more (two in the embodiment) second connection members 330 are provided in the circumferential direction (winding direction) of the first pipe body 300 and the second pipe body 310 and are fixed in a state in which the first pipe body 300 and the second pipe body 310 are disposed side by side. The second connection member 330 is provided with one or more (two in the embodiment) recessed portions 331 in which the first pipe body 300 is accommodated, and one or more (two in the embodiment) recessed portions 332 which are disposed on a side opposite to the recessed portions 331 and in which the second pipe body 310 is accommodated. The first pipe body 300 is pushed to be connected to the recessed portion 331 positioned on one side of the second connection member 330, and the second pipe body 310 is pushed to be connected to the recessed portion 332 positioned on a side opposite to the second connection member 330. In this manner, the second connection member 330 maintains an appropriate connection state between the first pipe body 300 and the second pipe body 310 which overlap each other in a direction along the center axis of the winding. Note that there is no particular limitation on the number of second connection members 330. In addition, there is no particular limitation on the number of recessed portions 331 and the number of recessed portions 332 which are formed in the second connection member 330. In addition, there is no particular limitation on the materials of the first connection member 320 and the second connection member 330.

As described above, in the storage case 290 according to the seventh embodiment, the second connection member 330 that connects the first pipe body 300 and the second pipe body 310 is separately provided from the first connection member 320 for maintaining the winding states of the first pipe body 300 and the second pipe body 310. Therefore, it is possible to detach the second connection member 330 such that the first pipe body 300 and the second pipe body 310 are separated from each other, with the winding states of the first pipe body 300 and the second pipe body 310 maintained by the first connection member 320, as necessary. After the first pipe body 300 and the second pipe body 310 are separated from each other, it is possible to take out the guiding catheter 70 and the inner catheter 80 from the first pipe body 300 and the second pipe body 310. The recessed portions 331 and the recessed portions 332 are positioned on a side opposite to the second connection member 330 when the connection is canceled by the second connection member 330, with the winding states of the first pipe body 300 and the second pipe body 310 maintained by the first connection member 320. Therefore, it is possible to cause the first pipe body 300 and the second pipe body 310 to move in only one direction in which the pipe bodies are separated from each other, and thus the operation is easily performed.

Figure 28:
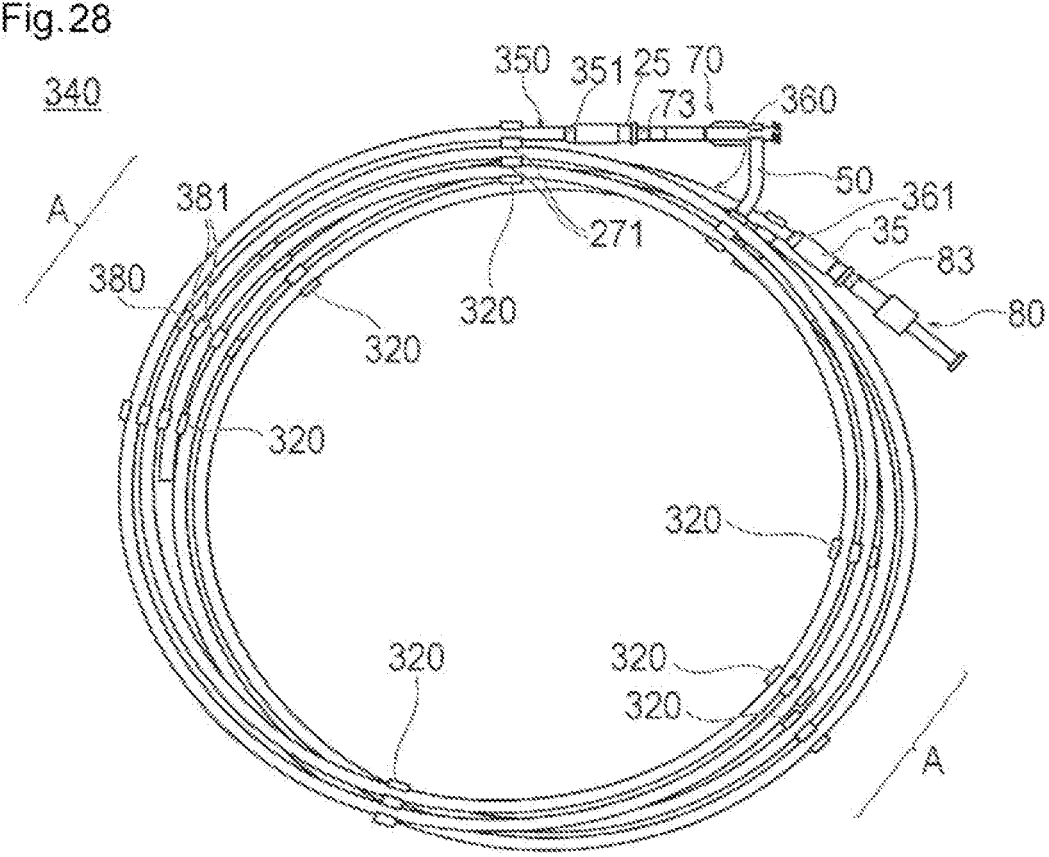
FIG. 28 is a plan view illustrating a storage case according to an eighth embodiment.

As illustrated in FIG. 28, a storage case 340 according to an eighth embodiment differs from the storage cases according to the first to seventh embodiments described above in that a first pipe body 350 and a second pipe body 360, which accommodate the medical elongated bodies, are disposed side by side such that the pipe bodies overlap each other in a state in which the center axis of the winding is deviated. Note that the same reference signs are assigned to the same portions common to those of the embodiments described above, and thus the description thereof is omitted.

The storage case 340 includes the first pipe body 350 (pipe body) that accommodates the guiding catheter 70, the second pipe body 360 (pipe body) that accommodates the inner catheter 80, the first connection member 320 (connection member) for maintaining shapes of the first pipe body 350 and the second pipe body 360, a second connection member 380 (connection member) that connects the first pipe body 350 and the second pipe body 360, and the package case 60 that holds the pipe bodies and members inside in the sterilized state.

The first pipe body 350 has a spiral shape as a whole, with a tube that extends to a predetermined length and is wound. The first pipe body 350 holds the guiding catheter 70 so as to store and carry the catheter with the guiding catheter 70 inserted through a first opening portion 351 (proximal opening portion) of the end portion that is positioned on the outer side of (opposite side on the center side of the winding) of the winding.

The second pipe body 360 has a spiral shape as a whole, with a tube that extends to a predetermined length and is wound. The second pipe body 360 holds the inner catheter 80 so as to store and carry the catheter, with the inner catheter 80 inserted through a second opening portion 361 (proximal opening portion) of an end portion that is positioned on the outer side of the winding. A winding direction (counterclockwise direction in FIG. 28) of the second pipe body 360 from the second opening portion 361 is the same direction as the winding direction of the first pipe body 350 from the first opening portion 351. The maximum outer circumferential diameters of the winding of the first pipe body 350 and the second pipe body 360 are substantially equal to each other. The first pipe body 350 and the second pipe body 360 are disposed to overlap each other in a direction along the center axis of the winding, in a state in which the center axes of the winding are deviated. There is no particular limitation on the materials of the first pipe body 350 and the second pipe body 360.

Several first connection members 320 are provided in the circumferential direction of the first pipe body 350 and the second pipe body 360, are fixed in a state in which adjacent tubes are arranged side by side from each other, and the first pipe body 350 and the second pipe body 360 maintain the spiral shape.

The second connection member 380 is provided with recessed portions 381 into which the first pipe body 350 or the second pipe body 360 is accommodated and which are disposed side by side. Both of the first pipe body 350 and the second pipe body 360 are inserted into the recessed portion 381 so as to be connected, and thereby the connection state between the first pipe body 230 and the second pipe body 240 is maintained. Note that the second connection member 380 according to the embodiment has the same structure (refer to FIG. 27A) as that of the first connection member 320, and the first connection member 320 may have a different structure. The center axes of the winding of the first pipe body 350 and the second pipe body 360 are deviated, and thereby the second connection member 380 is provided in a region A in which the tube of the first pipe body 350 and the tube of the second pipe body 360 do not overlap in the center axis direction of the winding. Note that two regions A are present on a side opposite to the circumferential direction, and the second connection member 380 is provided in one region A. Therefore, forced deformation of the first pipe body 350 and the second pipe body 360 is reduced such that the tube is positioned on the flat surface on both sides on the side opposite to the circumferential direction, and thus the winding surface is not bent. Hence, excessive deformation of the guiding catheter 70 and the inner catheter 80 inside the first pipe body 350 and the second pipe body 360 is reduced, and it is possible to reduce an increase in sliding resistance when the first pipe body 350 and the second pipe body 360 are pulled out from the first pipe body 350 and the second pipe body 360.

As described above, in the storage case 340 according to the eighth embodiment, the first pipe body 350 and the second pipe body 360 are disposed side by side so as to overlap each other in a state in which the center axes of the winding are deviated. Therefore, it is possible to easily connect the first pipe body 350 and the second pipe body 360 by the second connection member 380 in the region A in which the tubes of the first pipe body 350 and the second pipe body 360 are arranged side by side.

Figure 29:
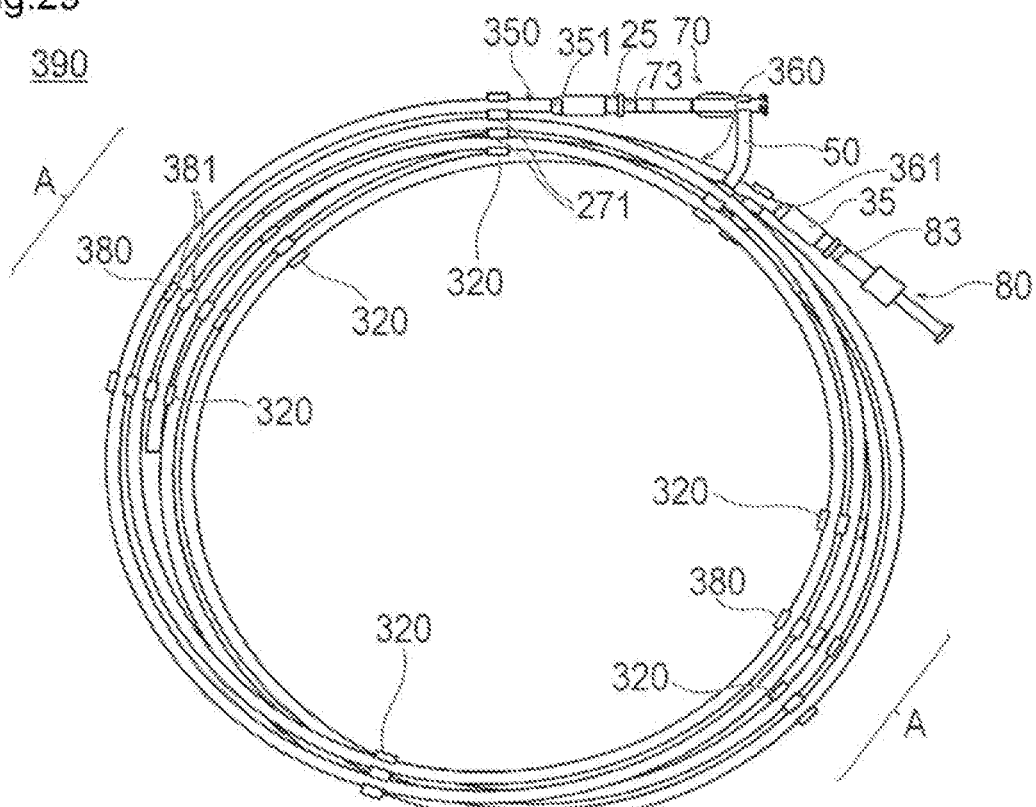
FIG. 29 is a plan view illustrating a storage case according to a ninth embodiment.
Figure 30:
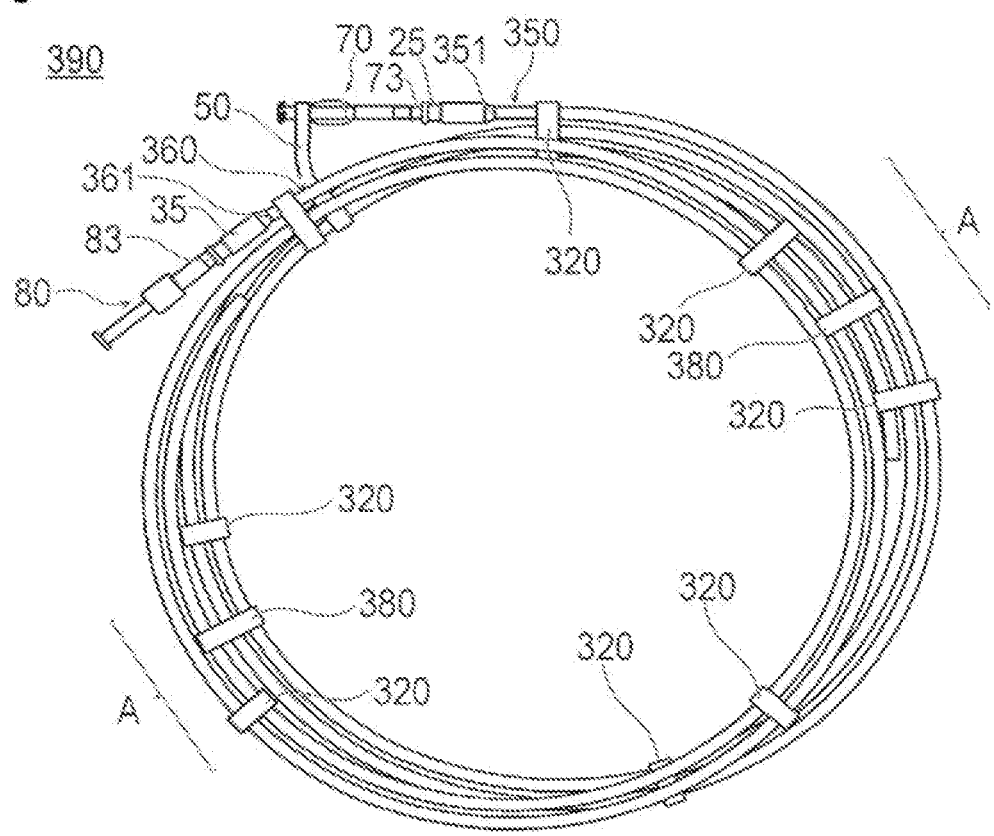
FIG. 30 is a plan view of the storage case illustrated in FIG. 29 when viewed from a back surface side.

As illustrated in FIGS. 29 and 30, a storage case 390 according to a ninth embodiment differs from the storage case 340 according to the eighth embodiment in that the two second connection members 380 are provided. Note that the same reference signs are assigned to the same portions common to those of the embodiments described above, and thus the description thereof is omitted.

In the storage case 390 according to ninth embodiment, the center axes of the winding of the first pipe body 350 and the second pipe body 360 are deviated, and thereby two regions A in which the tubes of the first pipe body 350 and the second pipe body 360 are arranged side by side are provided, and the second connection member 380 is provided in each of the region A. Therefore, the first pipe body 350 and the second pipe body 360 are strongly connected by the second connection member 380, and it is possible to sufficiently reduce the shift in the package case 60. In addition, when the storage case 390 according to the ninth embodiment is detached from the package case 60, it is possible to sufficiently reduce a concern that one of the pipe bodies will fall down.

Figure 31:
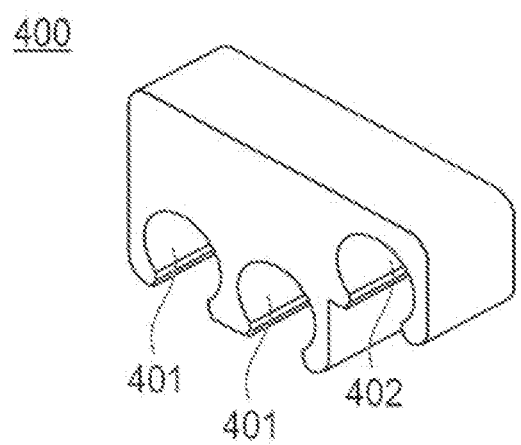
FIG. 31 is a perspective view illustrating a modification example of a second connection member according to the ninth embodiment.

In addition, the second connection member that connects the first pipe body 350 and the second pipe body 360 may be provided with a step such that a recessed portion 401 in which the first pipe body 350 is accommodated and a recessed portion 402 in which the second pipe body 360 is accommodated are positioned at different heights as a second connection member 400 as a modification example illustrated in FIG. 31. When the first pipe body 350 and the second pipe body 360 are connected by the second connection member 400 in two regions A positioned on a side opposite to the circumferential direction by using the second connection member 400 having such a configuration, the winding surface is appropriately maintained, and the winding surface is not bent. Hence, excessive deformation of the guiding catheter 70 and the inner catheter 80 inside the first pipe body 350 and the second pipe body 360 is reduced, and it is possible to reduce an increase in sliding resistance when the first pipe body 350 and the second pipe body 360 are pulled out from the first pipe body 350 and the second pipe body 360.

Figure 32:
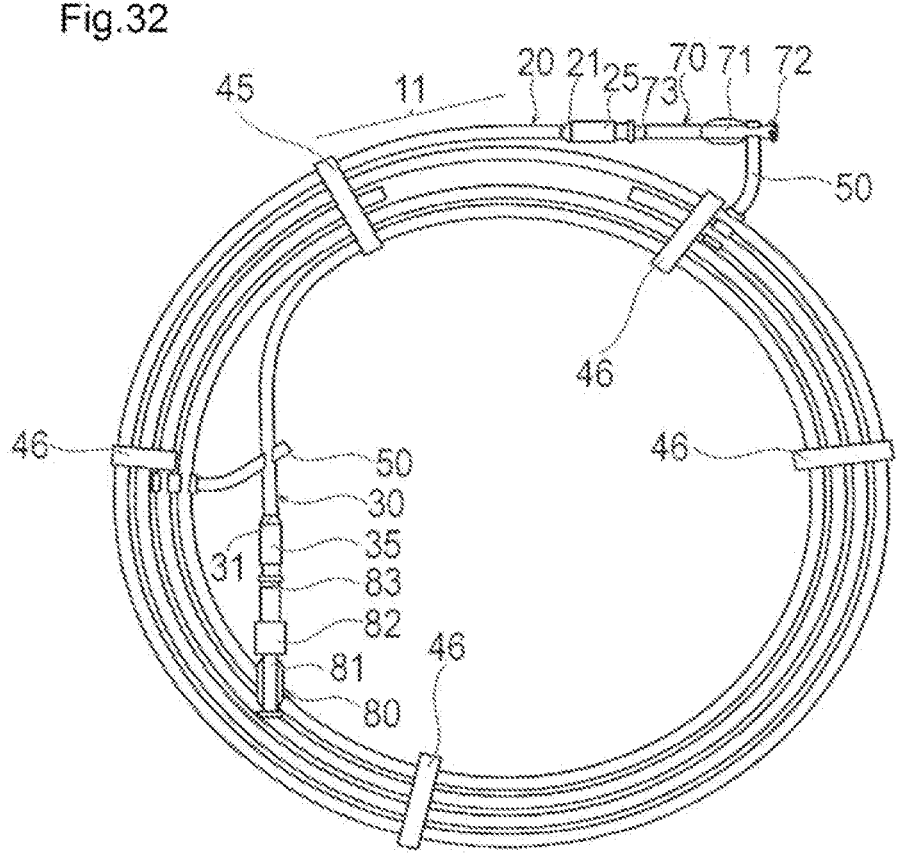
FIG. 32 is a plan view illustrating a modification example of the storage case according to the first embodiment.

In a modification example of the first embodiment illustrated in FIG. 32, among the plurality of connection members, the first connection member 45 that fixes the vicinity of the outer pipe opening portion 21 of the outer pipe body 20 and the inner pipe opening portion 31 of the inner pipe body 30 may have a color different from that of the second connection member 46. For example, it is possible to set the first connection member 45 in red, and the second connection member 46 in white. As described above, the grasp portion 11 is easily recognized with the first connection member 45 having a different color, and the operability improves.

Figure 33:
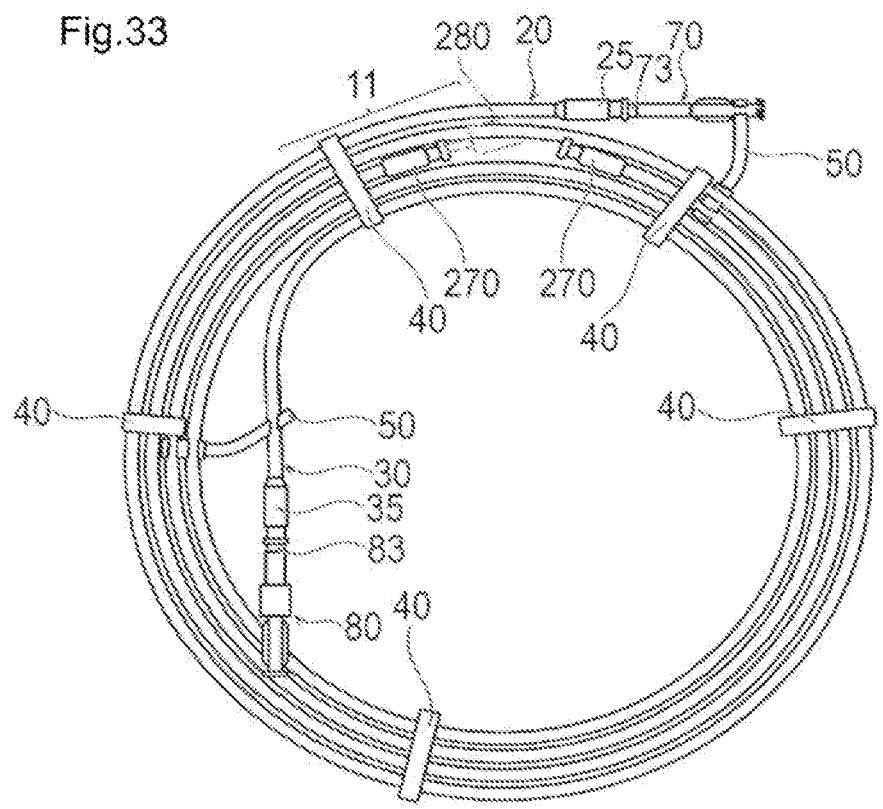
FIG. 33 is a plan view illustrating another modification example of the storage case according to the first embodiment.

In addition, as another modification example of the first embodiment illustrated in FIG. 33, a holder hub 270 into which a syringe 280 can be inserted is provided at an end portion (distal opening portion) on the side opposite to the side on which the outer pipe opening portion 21 of the outer pipe body 20 is formed, or an end portion (distal opening portion) on the side opposite to the side on which the inner pipe opening portion 31 of the inner pipe body 30 is formed. The holder hub 270 communicates with the lumens of the inner pipe body 30 or the outer pipe body 20, the syringe 280 is connected such that a liquid such as the physiological salt solution is injected from a syringe 280, and thereby it is possible to guide the liquid to the lumens of the inner pipe body 30 and the outer pipe body 20. In this manner, it is possible to wet lubricating coating provided on the outer peripheral surface of the inner catheter 80 in the inner pipe body 30, and on the outer peripheral surface of the guiding catheter 70 in the outer pipe body 20 such that it is possible to exhibit lubricating properties. Note that the holder hub 270 is not limited to only the first embodiment, and may be provided even on the pipe bodies of the second to ninth embodiments.

There is no particular limitation on the medical elongated bodies accommodated in the storage case, as long as the medical elongated bodies are assembled when used. For example, the medical elongated body may be a catheter for medical treatment (procedure) such as a guiding catheter and a balloon catheter, or may be a dilator or a sheath having a lumen into which a dilator can be inserted. In addition, there is no particular limitation on the number of medical elongated bodies and the pipe bodies which are accommodated in one package case.

The detailed description above describes features and aspects of embodiments of a storage case disclosed by way of example. The invention is not limited, however, to the precise embodiments and variations described. Changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. A method for inserting a catheter assembly into a vessel using a storage case in which an outer pipe body and an inner pipe body which accommodate a guiding catheter and an inner catheter are connected to each other, the method comprising:
   inserting a syringe into a hub portion of the guiding catheter, injecting a heparinized physiological salt solution, and priming the inside of the guiding catheter;
   inserting a syringe into a hub portion of the inner catheter, injecting a heparinized physiological salt solution, and priming the inside of the inner catheter;
   inserting a syringe into a holder hub provided on a side opposite to an insertion portion of the outer pipe body into which a catheter hub is inserted, the outer pipe body accommodating the guiding catheter with the holder inside out, injecting heparinized physiological salt solution, and priming an outer surface of the guiding catheter;
   grasping a grasp portion of the storage case with one hand;
   maintaining a state of grasping the grasp portion with the one hand while pulling out the inner catheter from the inner pipe body with the other hand;
   inserting the pulled-out inner catheter into a proximal opening portion of the guiding catheter;
   causing a locking rotation portion of the inner catheter to rotate and to be connected to a locking projection portion of the guiding catheter;
   assembling the guiding catheter and the pulled-out inner catheter;
   pulling-out, from the outer pipe body, the guiding catheter which is in a state where the inner catheter is assembled, with the hand that pulls out the inner catheter;
   taking out, from the storage case, a catheter assembly assembled by the guiding catheter and the pulled-out inner catheter; and
   inserting the catheter assembly into a vessel through a sheath inserted into the vessel in advance.

2. The method of claim 1, further comprising, before grasping the grasp portion, performing the steps of:
   inserting a syringe into a hub portion of the guiding catheter, injecting a heparinized physiological salt solution, and priming the inside of the guiding catheter;
   inserting a syringe into a hub portion of the inner catheter, injecting a heparinized physiological salt solution, and priming the inside of the inner catheter; and
   inserting a syringe into a holder hub provided on a side opposite to an insertion portion of the first pipe body into which a catheter hub is inserted, the first pipe body accommodating the guiding catheter with the holder inside out, injecting heparinized physiological salt solution, and priming an outer surface of the guiding catheter.

3. The method of claim 1, further comprising, before grasping the grasp portion, removing the storage case from a package case.

4. The method of claim 1, wherein the outer pipe body and the inner pipe body each define a center axis of winding, the center axis of winding of the outer pipe body and the center axis of winding of the inner pipe body deviating from one another.

5. The method of claim 1, wherein the outer pipe body and the inner pipe body do not overlap each other in two separate regions on opposite sides of the storage case, a first connection member connects the outer pipe body and the inner pipe body in a first one of the two separate regions, and a second connection member connects the outer pipe body and the inner pipe body in a second one of the two separate regions.

* * * * *